(12) United States Patent
Pemov et al.

(10) Patent No.: US 7,432,055 B2
(45) Date of Patent: Oct. 7, 2008

(54) DUAL PHASE MULTIPLEX POLYMERASE CHAIN REACTION

(75) Inventors: Alexander Pemov, Charlottesville, VA (US); Sergei Bavykin, Darien, IL (US)

(73) Assignee: UChicago Argonne LLC, Chicago, IL (US)

( * ) Notice: Subject to any disclaimer, the term of this patent is extended or adjusted under 35 U.S.C. 154(b) by 173 days.

(21) Appl. No.: 10/794,381

(22) Filed: Mar. 5, 2004

(65) Prior Publication Data

US 2005/0196760 A1    Sep. 8, 2005

(51) Int. Cl.
*C12Q 1/68* (2006.01)
*C12P 19/34* (2006.01)

(52) U.S. Cl. .......................................... 435/6; 435/91.2
(58) Field of Classification Search ........................ None
See application file for complete search history.

(56) References Cited

U.S. PATENT DOCUMENTS

| 5,641,658 | A | | 6/1997 | Adams et al. | |
|---|---|---|---|---|---|
| 5,888,723 | A | | 3/1999 | Sutton et al. | |
| 6,017,738 | A | | 1/2000 | Morris et al. | |
| 6,090,592 | A | | 7/2000 | Adams et al. | |
| 6,300,070 | B1 | * | 10/2001 | Boles et al. | ..................... 435/6 |
| 6,618,679 | B2 | * | 9/2003 | Loehrlein et al. | ............. 702/20 |
| 2005/0227263 | A1 | * | 10/2005 | Green et al. | .................... 435/6 |

OTHER PUBLICATIONS

Bing, David H. et al. (2003). Bridge Amplification: A solid phase PCT system for the amplification and detection of allelic differences in single copy genes. http://www/promega.com/geneticidproc/ussymp7proc/0726.htnl.

Tillib, Strizhkov and Mirzabekov, Integration of Multiple PCR Amplifications and DNA Mutation Analyses by Using Oligonucleotide Microchip, Analytical Biochemistry 292, 155-160 (2001), published online Apr. 2, 2001 http://www.idealibrary.com, United States.

Mikhailovich, Lapa, Gryadunov, Strizhkov et al., Detection of Rifampicin-Resistant Mycobacterium tuberculosis Strains by Hybridization and Polymerase Chain Reaction on a Specialized TB-Microchip, Bulletin of Experimental Biology and Medicine, vol. 131, No. 1, Jan. 2001, Plenum Publishing Corporation.

Strizhkov, Drobyshev, Mikhailovich and Mirazbekov, PCR Amplification on a Microarray of Gel-Immobilized Oligonucleotides: Detection of Bacterial Toxin- and Drug-Resistant Genes and Their Mutations, BioTechniques 29:844-957 (Oct. 2000), United States.

Yershov, Barsky, Belgovskiy, et al., DNA analysis and diagnostics on oligonucleotide microchips, Proc. Natl. Acad. Sci, USA, vol. 93, pp. 4913-4918, May 1996, United States.

Khrapko, Lysov, Khorlyn, et al., An oligonucleotide hybridization approach to DNA sequencing, FEBS Letters, vol. 256, No. 1,2, 118-122, Published by Elsevier Science Publishers B.V. (Biomedical Division) 1989 Federation of European Biochemical Societies.

Guschin, Yershov, Zaslavsky, et al., Manual Maufacturing of Oligonucleotide, DNA, and Protein Microchips, Analytical Biochemistry 250, 203-211 (1997) Article AB972209, Copyright 1997 by Academic Press, United States.

Proudnikov, Timofeev, Mirzabekov, Immobilization of DNA in Polyacrylamide Gel for the Manufacture of DNA and DNA-Oligonucleotide Microchips, Analytical Biochemistry 259, 34-41 (1998), Article No. AB982620, Copyright 1998 Academic Press, United States.

Jaschke, Furste, Nordhoff, et al., Synthesis and properties of oligodeoxyribonucleotide—polyethylene glycol conjugates, 4810-1817 Nucleic Acids Research, 1994, vol. 22, No. 22, Copyright 1994 Oxford University Press, United States.

Greg T. Hermanson, Bioconjugate Techniques, 8. Tags and Probes, pp. 324-326, Copyright 1996 by Academic Press, Inc. , United States.

Kelly, Chernov, Tovstanovsky, et al., Radical-generating coordination complexes as tools for rapid and effective fragmentation and fluorescent labeling of nucleic acides for microchip hybridization, Analytical Biochemistry 311 (2002) 103-118, available online at www.sciencedirect.com, Academic Press, United States.

Zlatanova and Mirzabekov, Gel-Immobilized Microarrays of Nucleic Acids and Proteins, Methods in Molecular Biology, vol. 170: DNA Arrays: Methods and Protocols (2001) Edited by: J.B/ Rampal, Copyright Humana Press, Inc., Totowa, NJ, United States.

* cited by examiner

*Primary Examiner*—Gary Benzion
*Assistant Examiner*—David C Thomas
(74) *Attorney, Agent, or Firm*—Barnes & Thornburg LLP; Alice O. Martin

(57) ABSTRACT

Highly specific and sensitive methods were developed for multiplex amplification of nucleic acids on supports such as microarrays. Based on a specific primer design, methods include five types of amplification that proceed in a reaction chamber simultaneously. These relate to four types of multiplex amplification of a target DNA on a solid support, directed by forward and reverse complex primers immobilized to the support and a fifth type—pseudo-monoplex polymerase chain reaction (PCR) of multiple targets in solution, directed by a single pair of unbound universal primers. The addition of the universal primers in the reaction mixture increases the yield over the traditional "bridge" amplification on a solid support by approximately ten times. Methods that provide multitarget amplification and detection of as little as $0.45$-$4.5 \times 10^{-12}$ g (equivalent to $10^2$-$10^3$ genomes) of a bacterial genomic DNA are disclosed.

22 Claims, 17 Drawing Sheets

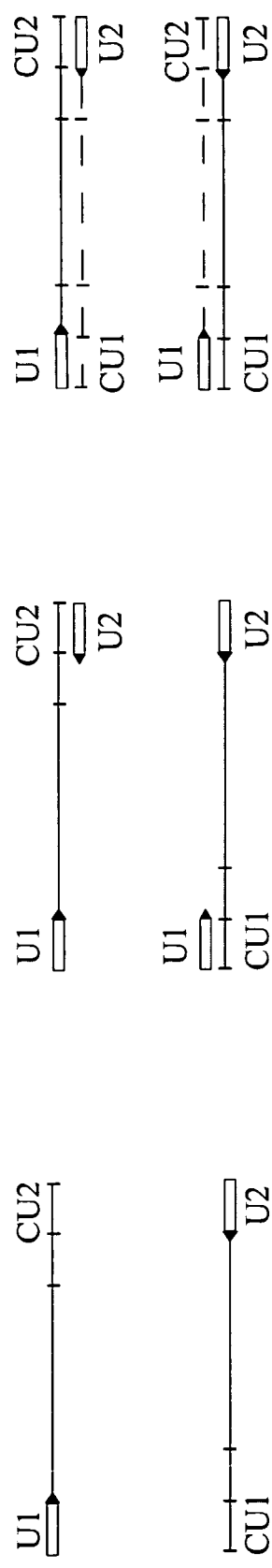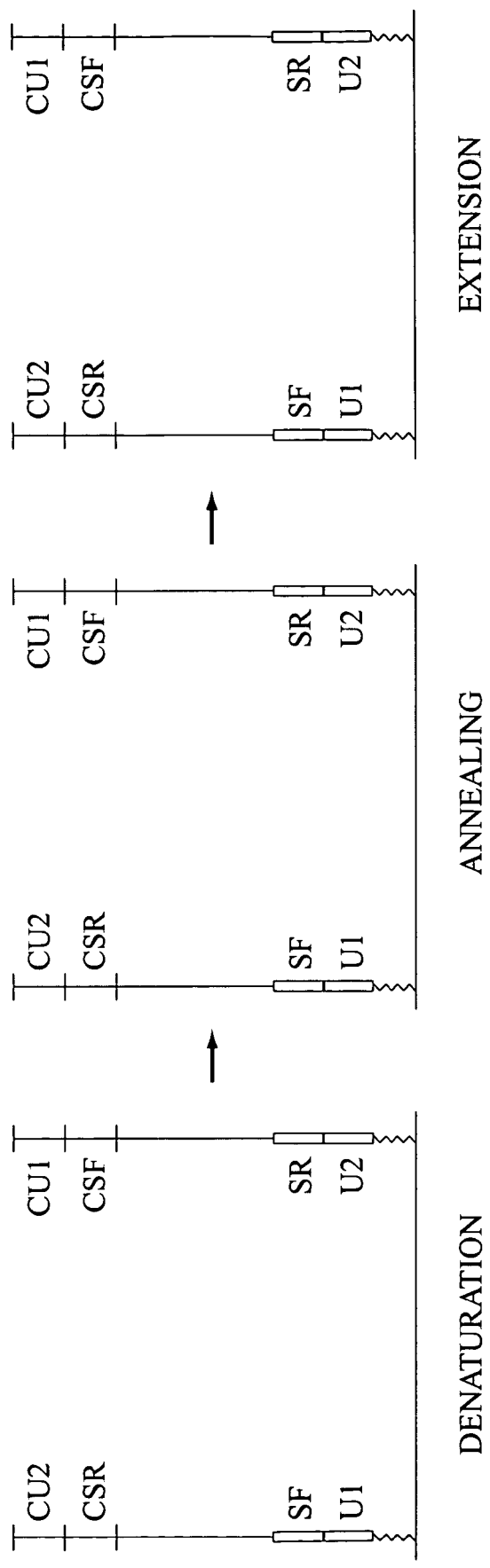
FIG. 3(D)

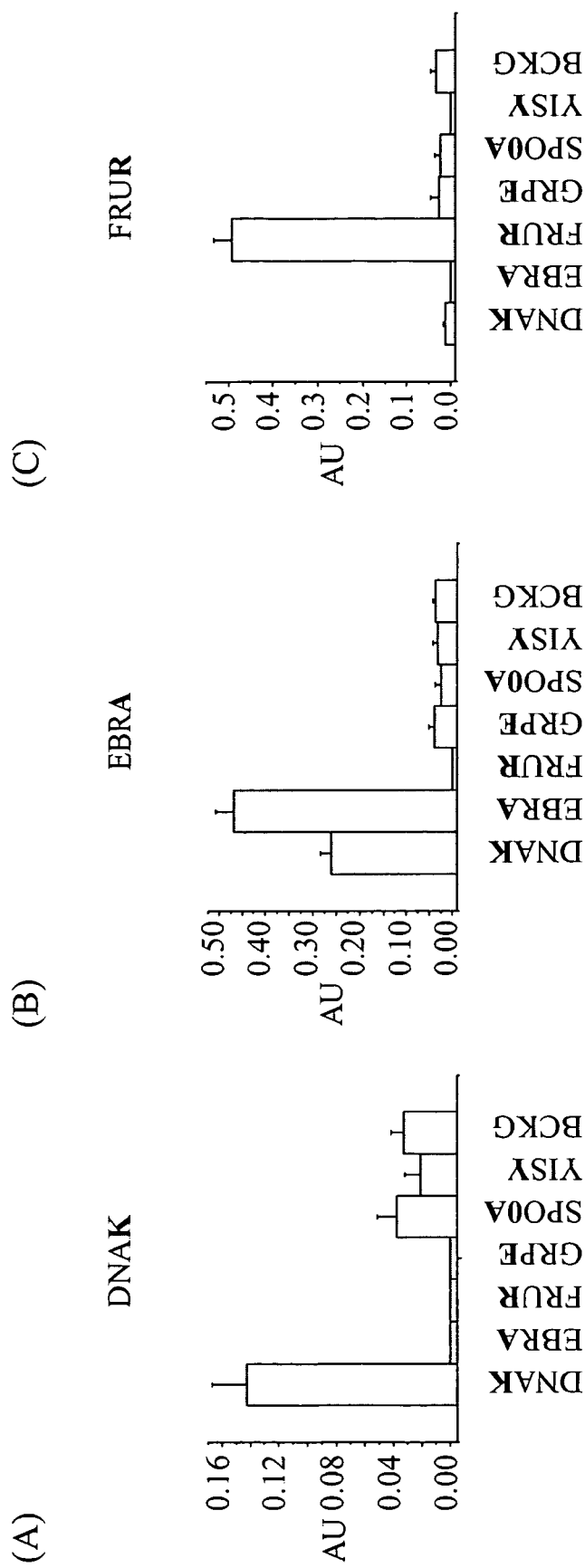
FIG. 9(A-C)

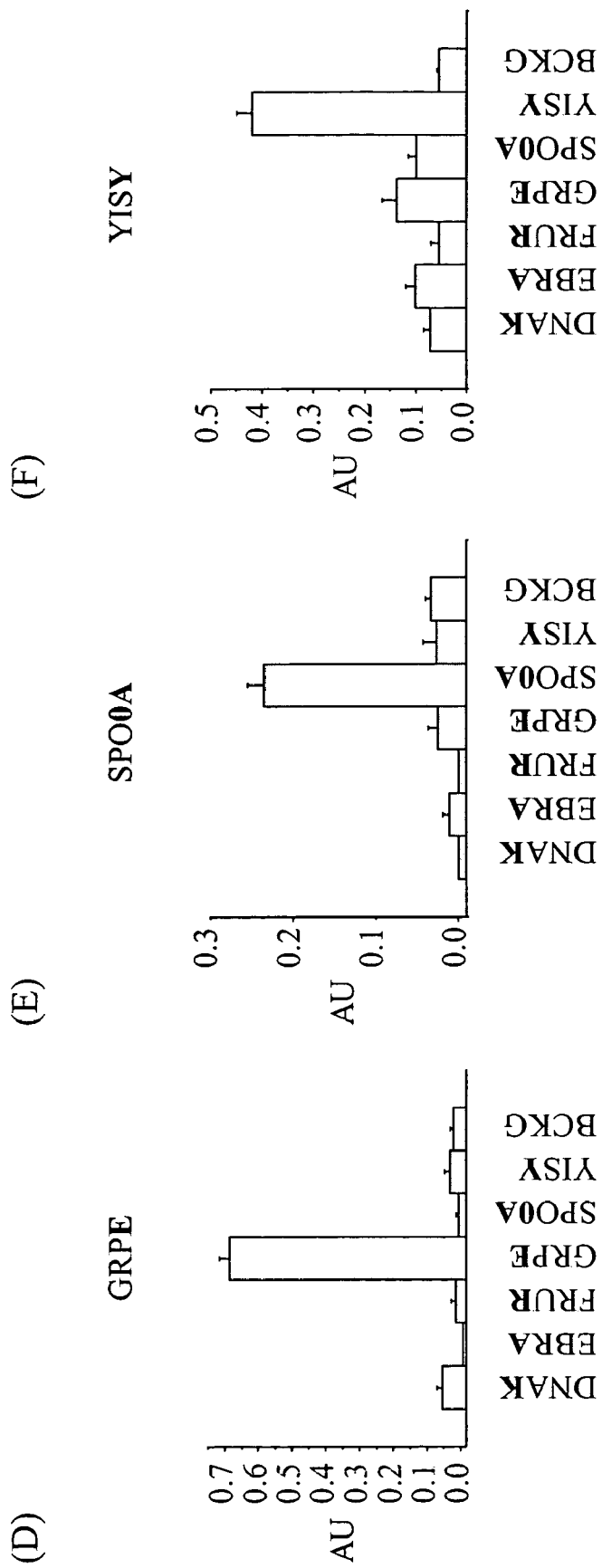
FIG. 9(D-F)

DUAL PHASE MULTIPLEX POLYMERASE CHAIN REACTION

The United States Government has rights in the disclosed invention pursuant to Contract No. W-31-109-ENG-38 between the U.S. Department of Energy (DOE) and the University of Chicago representing Argonne National Laboratory.

BACKGROUND

Hybridization of molecules in biological samples using microarrays allows analysis and detection of multiple nucleic acid targets simultaneously. However, limitations of the method include its relatively low sensitivity. Often the DNA target sequence of interest (i.e. the sequence which must be detected) is only present in low abundance. Usually, nucleic acid targets of low copy e.g. $10^3$, cannot be detected reliably by current methods.

Frequently, this necessitates the use of conventional polymerase chain reaction (PCR) techniques before the hybridization process, which restricts multiplicity. Several attempts have been made to amplify DNA targets by PCR directly on solid supports e.g., biochips, microbeads, and the like. However, these methods are either much less sensitive compared to that for conventional PCR, e.g. in tubes, or they can be used only for amplification of a very limited number of targets. Low sensitivity of PCR on solid supports may be merely due to the fact that, unlike the target, the primers are gathered in a volume that is much smaller than that of the reaction chamber so that only a small portion of the target can come into contact with the primers.

Some methods for performing PCR reactions on solid supports such as use on biochips or microbeads are not as sensitive as conventional PCR, or are restricted in the number of DNA sequences that can be detected. Moreover, often these methods require multiple steps and therefore are also slow, laborious, and expensive. Improved methods are needed.

SUMMARY OF THE DISCLOSURE

Methods to amplify a target nucleic acid molecule in a reaction chamber using complex and universal primers are disclosed.

Dual-phase multiplex amplification of nucleic acids in a reaction chamber includes amplification directed by multiple pairs of complex primers, immobilized to a support (e.g., biochip), and amplification directed by a single pair of universal primers in the liquid phase of a reaction chamber. Combination of amplification of target nucleic acid molecules on the surface of a support and in solution of a reaction chamber, results in an increased sensitivity compared to an amplification only on the surface of a support. Dual-phase amplification in a single reaction detects multiple distinct target nucleic acid molecules.

A method to amplify a target nucleic acid molecule in a sample includes the steps of:
(a) performing linear multiplex amplification of the target nucleic acid on a support with complex primers and universal primers to synthesize modified targets;
(b) releasing the amplified modified targets to a liquid phase;
(c) performing amplification of the target nucleic acid molecules in the liquid phase with universal primers; and
(d) annealing the amplified modified targets to the support wherein further linear amplification with complex primers occurs.

A method to amplify a target nucleic acid molecule in a sample includes the steps of:
(a) immobilizing a plurality of first and second complex primers to a support;
(b) annealing a single stranded target nucleic acid molecule to a specific segment of a first complex primer on the support;
(c) extending the first complex primer to synthesize a first complementary nucleic acid molecule on the support;
(d) forming a bridge from the first complementary nucleic acid molecule to a specific segment of a second complex primer on the support;
(e) extending the second complex primer to synthesize a second complementary nucleic acid molecule on the support;
(f) amplifying the first and second complementary nucleic acid molecules immobilized to the support using unbound universal primers to synthesize a plurality of modified targets;
(g) releasing the modified targets to a liquid phase of a reaction chamber;
(h) amplifying the modified targets in the liquid phase of the reaction chamber using unbound universal primers; and
(i) annealing the unattached modified targets to the first and second complex primers in the support wherein further amplification occurs.

The first complex primer includes a segment complementary to the target nucleic acid molecule and a universal segment. The second complex primer includes a segment complementary to the first complementary target nucleic acid molecule and a universal segment. The universal primers include sequences specific to the sequences of the universal segments of the complex primers.

The plurality of first and second complex primers include segments that are complementary to a plurality of target nucleic acid molecules.

The first and the second complex primers are immobilized to an attachment site that is spatially separated from other pairs of primers.

The first complex primer may be designated as a forward primer and the second complex primer may be designated as a reverse primer.

A method of detecting the amplified nucleic acid molecules in the support includes detecting the annealed amplified molecules in the support with a probe. The probe is selected from nucleic acids, antibodies, and peptides labeled with radioactive isotopes, gold particles, light scattering particles, energy transferring compounds, fluorescent dyes, or luminescent dyes. The probe may be targeted toward any segment of the amplified nucleic acid molecules.

The first and second complex primers are about 10 to 100 bases long and the universal primers are about 5 to 95 bases long.

The liquid phase of the reaction chamber is in contact with the support that includes immobilized complex primers.

A method of detecting the amplified nucleic acid molecules in the support includes the steps of:
(a) incorporating labeled nucleotides during nucleic acid amplification; and
(b) detecting the labeled nucleotides in the amplified nucleic acid molecules.

The labeled nucleotides include labels such as fluorescent, luminescent, radioactive, and immunological labels.

The support may include glass, microbeads, microcanals, gel pads, membranes, metal, plastic and any suitable matrix.

A module includes a support to which a plurality of complex primers are attached, wherein the complex primers comprise a 5'-universal segment and a 3'-segment specific to a target nucleic acid molecule, and a reaction chamber comprising a plurality of universal primers. The universal primers include a segment specific to the 5'-universal segment of the complex primers. The reaction chamber is in contact with the support.

A microarray includes a support with a plurality of attachment sites, wherein a first attachment site includes a plurality of tethered forward and reverse complex primers, wherein the forward complex primer includes a 5'-universal segment identical to a 5'-universal segment of the forward complex primer in a second attachment site and a 3'-segment specific for a first target nucleic acid molecule, and the reverse complex primer includes a 5'-universal segment identical to a 5'-universal segment of the reverse complex primer in a second attachment site and a 3'-segment specific for the first target nucleic acid molecule.

The plurality of attachment sites in a microarray may include tethered complex primers with the 3'-segments specific for a plurality of target nucleic acids. An attachment site may also contain more than one type of primers. The tethered complex primers may include linkers. The support in a microarray may include glass, microbeads, microcanals, gel pads, nylon membranes, metal, and any suitable matrix.

A diagnostic kit includes in discrete compartments the following constituents:
(a) a support that includes a plurality of attachment sites bearing tethered complex primers;
(b) a reaction chamber; and
(c) a plurality of universal primers.

The diagnostic kit may also include a polymerase for amplification, labeled and non-labeled nucleotides.

A method to amplify a target nucleic acid molecule in a sample using a combination of a plurality of universal primers present in a solution and a plurality of complex primers immobilized to a solid support, wherein the complex primers include a 5'-universal segment and a 3'-segment specific to a target nucleic acid in the sample includes the steps of:
(a) annealing the target nucleic acid molecule reversibly to the solid support via hybridization of the 3'-specific segment of a first immobilized complex primer to the target nucleic acid, where an extension of the first complex primer results in a linear amplification of the target nucleic acid molecule and an irreversible binding of the amplified target nucleic acids to the solid support through the first complex primer;
(b) forming a bridge between extended first complex primer bound in the solid support and a second complex primer via hybridization of the complementary sequences of the extended first complex primer and a 3'-segment of the second complex primer followed by extension of the second complex primer, resulting in further amplification of the target nucleic acid;
(c) amplifying the extended first and second complex primers bound to the support using universal primers to synthesize a plurality of modified targets;
(d) releasing the amplified modified targets to the solution, wherein further pseudo-monoplex amplification with universal primers occurs; and
(e) annealing 3'-end regions of the amplified modified targets in solution to the complex primers attached to the solid support resulting in further linear amplification of the modified targets bound to the support.

The plurality of complex primers comprise 3'-segments that are specific to a plurality of different target nucleic acid molecules. The universal primers comprise nucleotide sequences that are at least partially identical to the 5'-universal segment of the complex primer. The plurality of universal primers comprise more than one specific sequence.

Further detection of the amplified target nucleic acid molecules bound to the solid support can be performed via hybridization with probes bearing a label that may include fluorescent dyes, luminescent dyes, radioactive isotopes, immunological markers, gold particles, beacon labels, light scattering labels, energy transfer labels.

Definitions

Amplicon: a DNA fragment of definite size and nucleotide sequence, generated by an amplification process such as polymerase chain reaction (PCR).

Annealing: providing conditions to allow complementary nucleic acid molecules to hybridize.

Array: molecules connected to a matrix or support in a specific arrangement relative to each other.

Attachment site: position in a support where one or more types of oligonucleotides or polynucleotides are attached.

Biochip: also known as a chip, DNA chip, DNA microarray, microchip, peptide chip or peptide array; includes array of biological molecules such as DNA fragments, peptides, proteins, lipids, and tissues connected to a matrix (small flat support).

Bridge amplification: amplification on a support, where both forward and reverse primers are immobilized to the support. The amplification proceeds through a formation of intermediate structures between the immobilized extended and un-extended primers. As disclosed herein, "bridge" is formed by annealing of the complementary sequences in the immobilized extended complex primer and immobilized un-extended complex primer in the support.

Extended primer: product of PCR; DNA fragment that includes the primer and a newly synthesized DNA.

Gene: DNA fragment that is responsible for the reproduction of specific biological molecules, mostly proteins, polypeptides and RNA. A "gene" referred to herein also includes regulatory regions (promoter and terminator), coding part and, in case of eukaryotes, introns.

Hybridization: the formation of duplex molecules from complementary single stranded nucleic acids, DNA and RNA. In the case of mycroarrays, a single stranded nucleic acid molecule is generally labeled, e.g. with a detectable dye (radioactive, fluorescent, and the like) and used as a target that may anneal to probes with similar sequences that are single stranded and attached to a solid support.

Immobilize: a process by which molecules are applied, fixed, printed, impregnated, or tethered to a support.

Linear amplification: amplification on a solid support where the annealing complex is created between unattached soluble target nucleic acids and one (forward or reverse) of the immobilized primers.

Matrix: a support such as glass slide, silicon, gold slide, gel pad, nylon membrane or other similar structures on which an array or microarray of molecules is formed. A matrix or support may contain functional groups to attach biomolecules.

Microarray: set of molecules immobilized on a biochip, microbeads, in microcanals, and the like.

Modified target: double or single stranded DNA amplification product, where a specific central part is flanked on one side by a sequence that is identical to one of the two universal primers, and flanked on the other side by a sequence that is complementary to the other of the two universal primers.

Nucleic acids: biological polymers with monomers represented by nucleotides. Nucleic acids presented by DNA and RNA.

Oligonucleotide: single stranded DNA or RNA molecule with any length ranging from four to 100 nucleotides.

PCR: polymerase chain reaction; used for amplification of nucleic acids.

Planar microarray: refers to a microarray organized on a two dimensional support.

Polynucleotide: any single stranded or double stranded molecule with a sequence of more than about one hundred nucleotides.

Primer: oligonucleotide capable of hybridizing to a complementary part of nucleic acid molecule and provides a free 3'OH group which can be extended by DNA or RNA polymerases.

Complex: primer that comprises two segments—specific and universal, and is immobilized to the surface of a support.

Forward: primer that may bind to a non-coding strand.

Reverse: primer that may bind to a complementary coding strand.

Universal: primer that may be identical or similar in its nucleotide sequence to a universal segment of a complex primer.

Pseudo monoplex amplification: refers to a PCR by which multiple modified DNA targets, flanked with a single pair of universal sequences, are amplified simultaneously with a single pair of universal primers.

Reaction chamber: refers to an enclosure where amplification is carried out; may include a support such as a biochip, reaction mix, and a cover slip or a gasket for increasing reaction volume.

Releasing: a process by which a hybridized molecule is separated and discharged to a liquid phase of a reaction chamber.

Reporting Probe: a labeled oligonucleotide with a nucleotide sequence complementary to the immobilized PCR product of interest.

Sample: includes bodily fluids such as blood, urine, saliva, etc., tissues (e.g. skin, muscles, etc.), microorganisms (e.g. bacteria, viruses, etc.) and environmental samples such as air, food, water and soil.

Sequence similarity: refers to the sequence similarity of nucleic acid molecules, which permits annealing or hybridization of two or more nucleic acids.

Tethered: attached, linked.

BRIEF DESCRIPTION OF THE DRAWINGS

FIG. 9 shows that multiplex dual-phase PCR is highly specific (A-F).

DETAILED DESCRIPTION OF THE DISCLOSURE

A new method for amplification of target nucleic acids by the polymerase chain reaction (PCR) on a solid support, e.g. a biological microchip or biochip, eliminates the need for a separate PCR step. Due to the primer design, the PCR reaction occurs both on a solid support and in a liquid phase of the reaction chamber, i.e. in solution.

Highly efficient, free volume PCR compensates for the low efficiency of PCR on a solid support, resulting in much higher overall efficiency of the PCR reaction on a solid support. The specific primer design allows multiplex PCR to be performed on a support, i.e., to amplify and detect multiple DNA targets in a single reaction on a single support.

In an embodiment, tethering pairs of complex primers on separate gel pads provide the possibility to perform multiple PCR reactions without the problem of primer dimerization. Using the methods disclosed herein, as little as 1,000 copies of target DNA present in the experimental sample were detected.

A method for multiplex DNA amplification on a solid support was developed. In light of the fact that multiplex PCR is severely inhibited by high concentration of primers in the reaction mix and by interference of primers from different pairs with each other, different primer pairs were spatially separated by tethering them to a solid support. PCR on a solid support is less efficient than the conventional type of PCR in which all components are dissolved in the reaction cocktail. To circumvent this obstacle a system was implemented in which multiplex PCR on a solid support is enhanced by pseudo monoplex PCR in the liquid phase of a reaction chamber. In this method the two types of primers—complex and universal—work in concert.

1. Primer Design.

Figure 1:
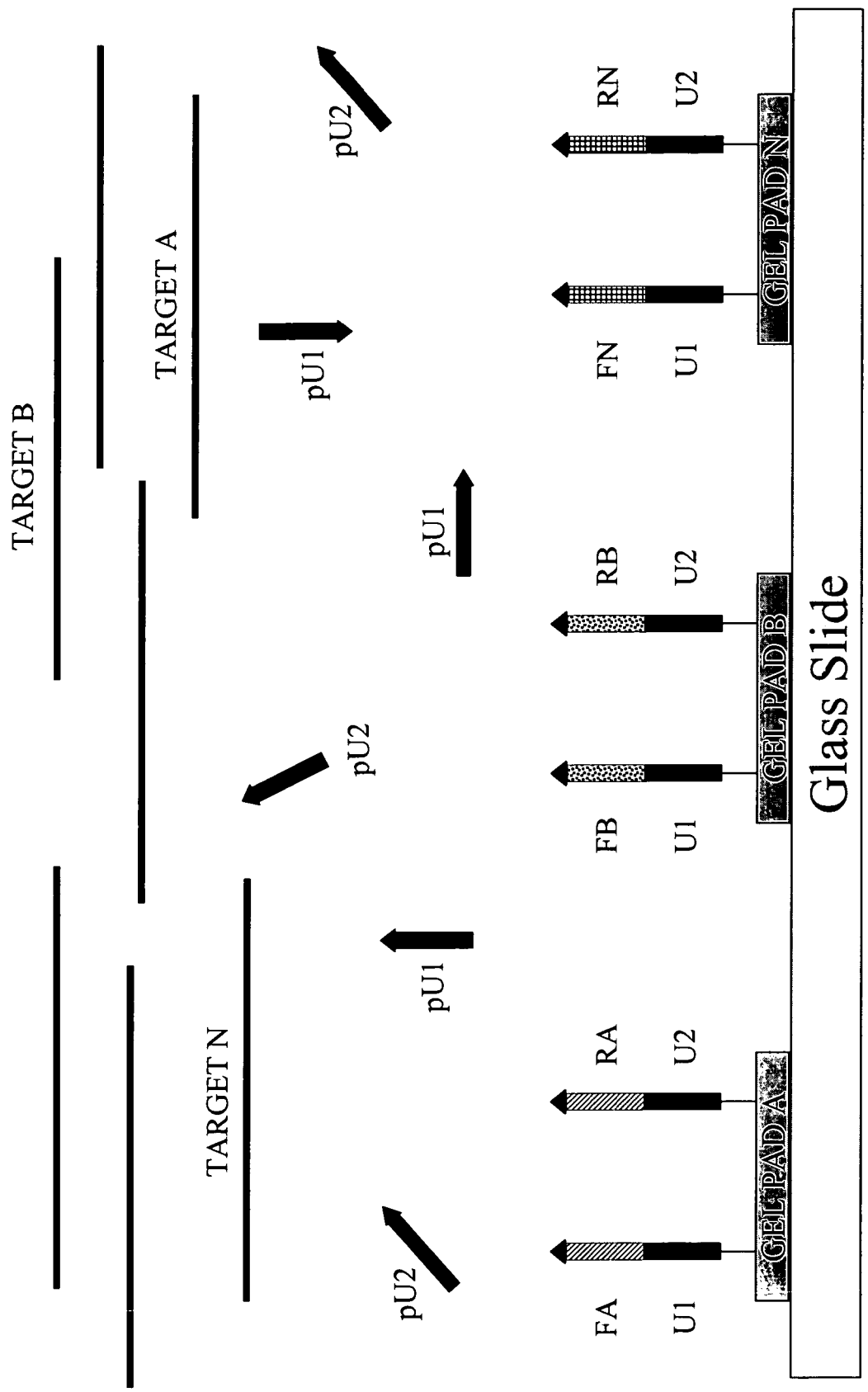
FIG. 1 illustrates the design of the primers and other components of the amplification process.

FIG. 1 illustrates the design of the primers and other components of the amplification process and a schematic representation of a 3-D biochip. Three major components of the amplification process reaction are depicted as follows: complex primers immobilized in the gel pads, universal unbound primers and target DNA. Three gel pads with immobilized complex primers are shown in the illustration: pad A, pad B and pad N. Immobilized complex primers U1-FA and U2-RA on Pad A; U1-FB and U2-RB on Pad B; and U1-FN and U2-RN on Pad N are shown.

Each complex immobilized primer includes two segments—specific and universal. Specific segments of complex primers are indicated by patterned fills. "F" designates forward specific segments of complex primers; and "R" designates reverse specific segments of complex primers, i.e. -FA and -RA designate forward and reverse segments of complex primers, respectively, and are immobilized to Pad A; -FB and -RB designate forward and reverse segments of complex primers, respectively, and are immobilized to Pad B and so forth.

Universal segments, U1 and U2, are shown in black. Universal segments U1- on all forward primers are the same, as well as universal segments U2- are the same on all reverse primers. A pair of unbound universal primers, pU1 and pU2; and target DNA, Target A, Target B, and Target N are shown as well. Specific segments of complex immobilized primers and the targets, which match to them, are shown by the same patterns. Primers are drawn as rectangles with black arrowheads representing their 3'-OH ends. Template DNA is shown as patterned horizontal lines. Solid grey lines indicate DNA fragments, which do not comprise sequences matching with primers immobilized on the support. Linkers that tether complex primers to the gel pads are shown as thin vertical lines. The first type of primers are 'complex primers', and the second type: 'universal' primers. Immobilized complex primers (U1-FA and U2-RA, U1-FB and U2-RB, U1-FN and U2-RN) are designed to be from 10 to 100 nucleotides long. They are covalently bound to the biochips. The universal primers (pU1 and pU2) are designed to be from 5 to 95 nucleotides long and are dissolved in the reaction mix. Complex primers comprise two segments—universal (U1- and U2-), and specific (FA- and RA-, FB- and RB-, FN- and RN-). The specific segments are designed as regular primers for conventional PCR, so that specific segments of complex primers immobilized to gel pad A, FA- and RA-, would direct amplification of target A; specific segments of complex primers immobilized to gel pad B, FB- and RB-, would direct amplification of target B, and so on. The universal segments U1- and U2- are both identical in their nucleotide sequences to those of the universal primers pU1 and pU2, respectively.

Figure 2A:
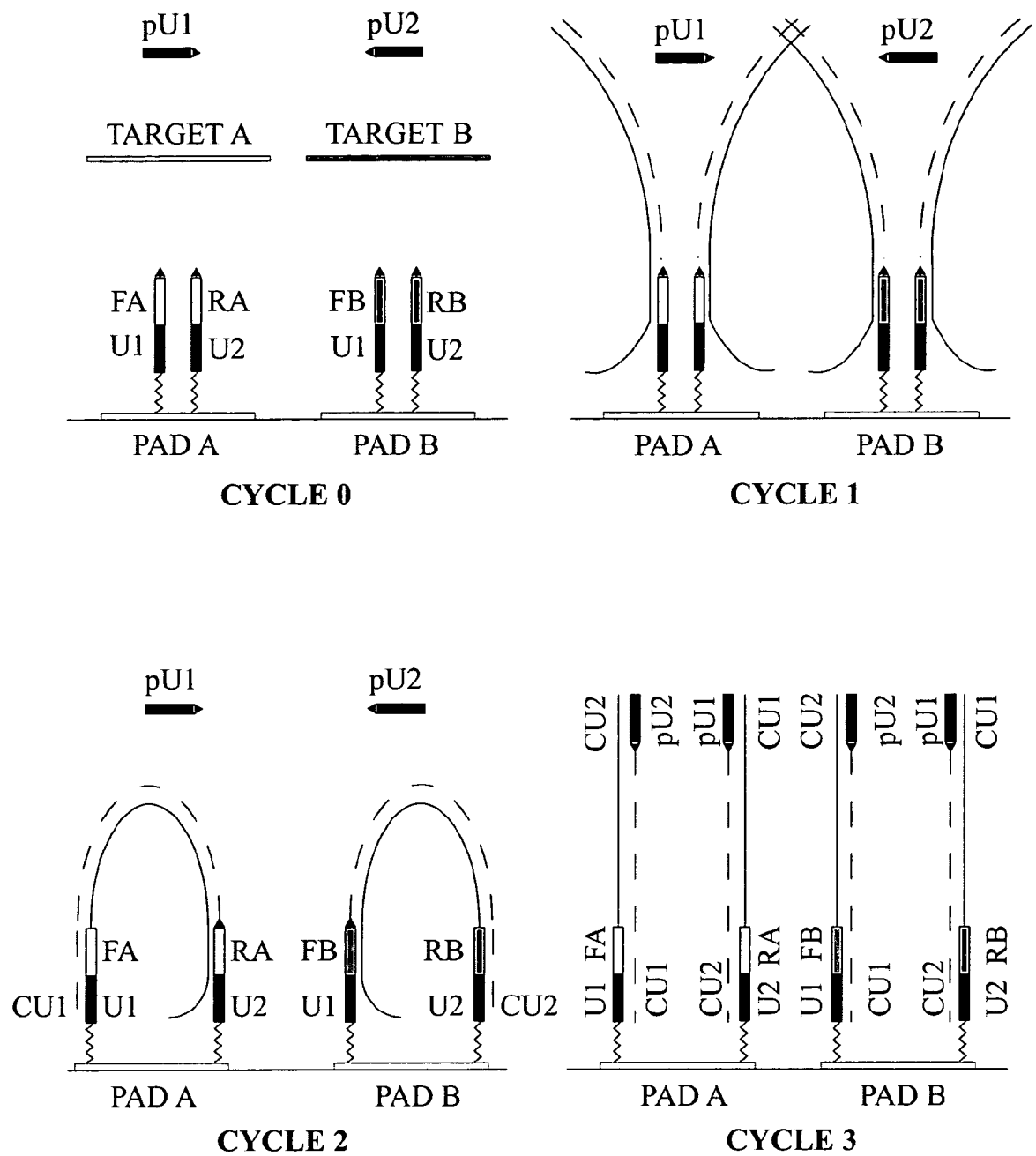
FIG. 2 shows a schematic representation of dual-phase multiplex PCR with complex primers bound to the gel pads and a pair of unbound universal primers.

Alternatively, the universal primers could contain additional nucleotides on their 5'- and 3'-ends and/or single nucleotide substitutions in the region overlapping with the universal primers. The function of the universal segments is to modify different PCR products, so that by the end of cycle 3, each product, which is being amplified in the reaction, is flanked by these universal sequences (see FIG. 2(A)). There are only two universal sequences incorporated into different complex primers. The first universal sequence (U1-) is tethered to the 5'-ends of specific segments of all forward complex primers (FA-, FB-, FN-), and the second universal sequence (U2-) is tethered to the 5'-ends of specific segments of all reverse complex primers (RA-, RB-, RN-). When present on their own, the universal sequences serve as universal primers. The number of different complex primer pairs immobilized to a microarray may equal the number of targets to be amplified and detected in the reaction, but there is only one pair of universal primers in the reaction (FIG. 1).

2. Schematic Representation of PCR on a Chip with Complex Primers Bound to the Gel Pads and a Pair of Universal Unbound Primers.

Figure 2B:
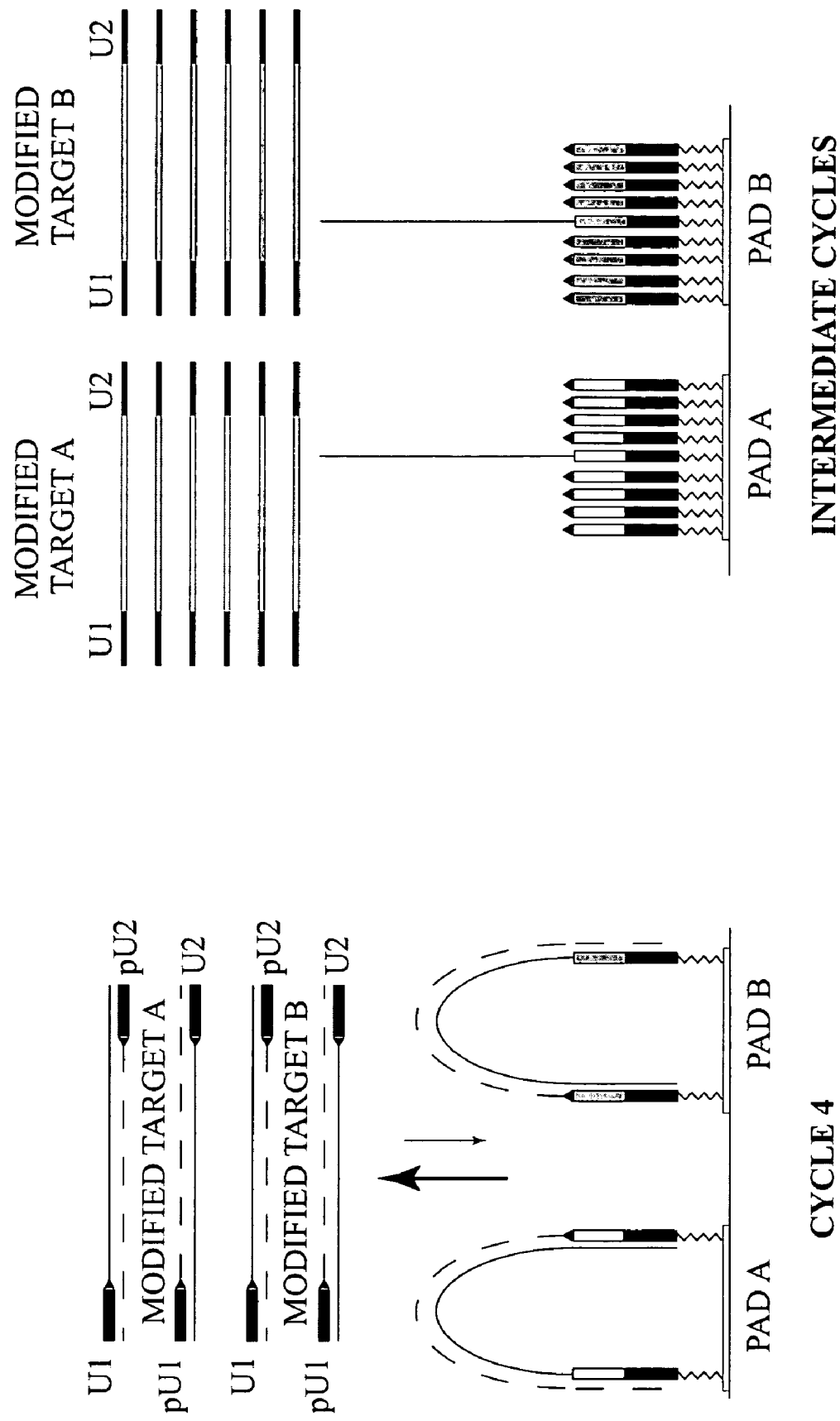
Figure 2C:
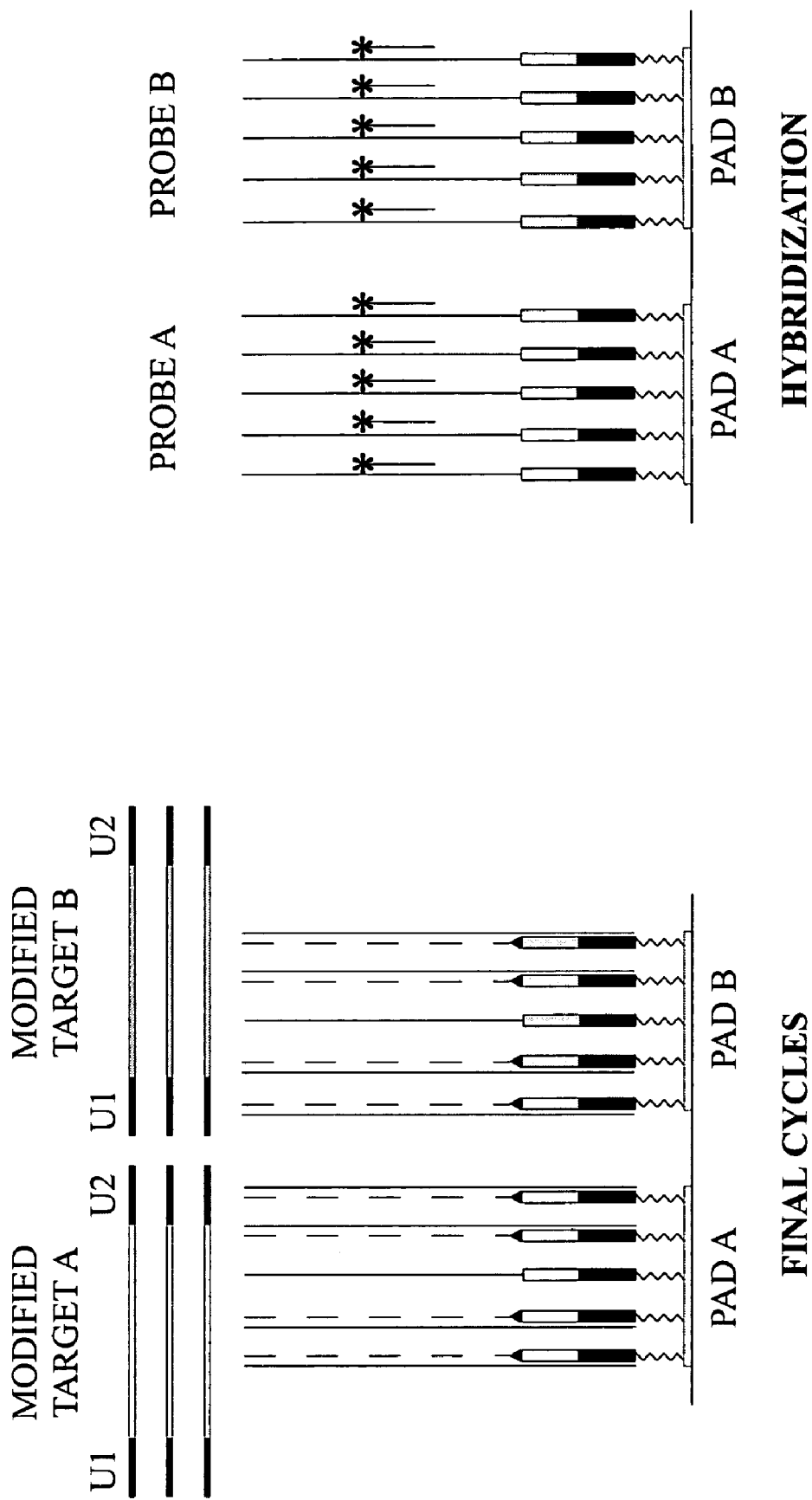

FIG. 2 shows a schematic representation of PCR on a chip with complex primers bound to the gel pads and a pair of unbound universal primers. (A) The reaction condition prior to the start of the reaction (Cycle 0) and the first three cycles (Cycle 1, Cycle 2, Cycle 3) are depicted. Two gel elements (Pad A and Pad B) with immobilized complex primers, U1-FA and U2-RA on Pad A, and U1-FB and U2-RB on Pad B, are shown. A pair of unbound universal primers, pU1 and pU2, and a target DNA, Target A and Target B, are shown as well.

In Cycle 1, target A anneals to the specific segments of immobilized complex primers U1-FA and U2-RA, target B anneals to the specific segments of immobilized complex primers U1-FB and U2-RB; the DNA polymerase extends the immobilized primers. Because the tethered primers are extended, the amplification products are also covalently bound, i.e. immobilized, to the gel elements of the support.

On-chip "bridge" amplification is depicted in Cycle 2. The immobilized primers, which were extended in Cycle 1, anneal to other complex primers, which did not participate in the reaction in the previous cycle, creating "bridges". The immobilized forward extended primers anneal to the immobilized complex reverse primers, and immobilized reverse extended primers anneal to the immobilized complex forward primers.

During extension phase of the thermal cycle, DNA polymerase extends the immobilized primers. For illustration, only one extended primer on each pad is shown. The immobilized extended primers, which were extended in Cycle 2, are now flanked by CU1 and CU2 sequences, which are complementary to U1 and U2, respectively. Immobilized forward extended primers are flanked by CU2 sequences at their 3'-ends; and immobilized reverse extended primers are flanked by CU1 sequences at their 3'-ends.

In Cycle 3, unbound universal primers pU1 and pU2 anneal to their complementary sequences CU1 and CU2, respectively; the DNA polymerase extends the primers, producing nascent DNA strands flanked either by U2/CU1 or U1/CU2 sequences (modified targets).

(B) In Cycle 4, in addition to the reaction occurring on the surface (as depicted for Cycle 1, Cycle 2 and Cycle 3), the amplification occurs in the solution phase of the reaction chamber.

A single pair of universal primers pU1 and pU2 directs the amplification of different modified targets. Two arrows, large and small, reflect the fact that due to the greater efficiency of PCR in solution as compared with PCR on a solid support, amplification in solution would be predominant. As an illustration, only bridge amplification on the solid support is shown. At midpoint of the reaction (Intermediate Cycles), there would be relatively few PCR products immobilized to the surface compared to the amount of soluble PCR products (Modified Targets A and B). (C) In the final third part of the reaction (Final Cycles), increased amount of the modified targets increase the amplification on the surface. Modified targets anneal to the immobilized primers, and DNA polymerase extends the primers. After the amplification process, the microarrays are washed and the immobilized PCR products are analyzed by hybridization of the microarray with internal reporting probes—fluorescently labeled oligonucleotides that specifically recognize the PCR products and not the primers (Hybridization).

Primers are shown as short rectangles with arrowheads. DNA targets are denoted as thin, long rectangles. Parental and nascent DNA strands are marked by solid and dashed lines, respectively. Linkers tethering complex primers to the gel elements are designated by zigzags. Reporting hybridization probes are labeled as short vertical lines with an asterisk on top. Universal primers pU1 and pU2 and universal segments of complex immobilized primers, U1 and U2, are shown in black. Target A and specific segments of complex primers on Pad A, -FA and -RA are specified by short blank rectangle. Target B and specific segments of complex primers on Pad B, -FB and -RB, are denoted as grey rectangles. CU1 and CU2 denote the sequences complementary to U1 and U2, respectively.

Cycle 0. As an illustration, only two gel pads, Pad A and Pad B, of a 3D microarray are shown (FIG. 2(A)). Each gel element contains a pair of complex immobilized primers, forward and reverse. Pad A contains primers U1-FA (forward) and U2-RA (reverse), and Pad B contains primers U1-FB (forward) and U2-RB (reverse). The primers are tethered via their 5'-ends to flexible linkers, which in turn are chemically bound to gel elements. A reaction chamber is filled with a reaction mix, containing thermostable DNA polymerase, buffer, dNTPs, target DNA and a pair of universal primers pU1 and pU2. For the sake of simplicity, only two targets, Target A and Target B, are shown.

Cycle 1. PCR starts on a surface (FIG. 2(A)). After heat induced DNA denaturation, single stranded targets anneal to corresponding immobilized primers, so that the strands of DNA Target A anneal to FA- or RA-segments of the complex primers immobilized to Pad A, and the strands of DNA Target B anneal to FB- or RB-segments of the complex primers immobilized to Pad B. DNA polymerase extends the primers. Newly synthesized, nascent, DNA is shown by dashed lines. Neither the universal segments U1- and U2-, nor universal primers pU1 and pU2 are involved in the amplification process yet.

Cycle 2. Primers, which were extended in the first cycle, bridge out to the primers, which did not participate in the reaction in the previous cycle: on-chip "bridge" amplification (FIG. 2(A)). The events of the first cycle are repeated in the second one, and a new type of event occurs. In every subsequent cycle, all types of the molecular interactions that took place in the previous cycles could be repeated. As an illustration, only new type of molecular events occurring on the surface of the microarray and in the PCR chamber are discussed and depicted in the drawings. The immobilized primers that were extended in the first cycle reach out to the primers, which did not participate in the previous cycle, forming "bridges": immobilized forward extended primers form "bridges" with immobilized complex reverse primers; and immobilized reverse extended primers form "bridges" with immobilized complex forward primers. During an extension phase, the synthesis of the nascent DNA strands proceeds also through the universal segments of the complex primers U1- and U2-. As result, forward and reverse primers, which were extended, now contain sequences complementary to U2 and U1, denoted as CU2 and CU1, respectively, at their 3' ends. Note that in the second cycle, universal primers pU1 and pU2 are still not involved into the reaction, so that amplification occurs on the surface via mechanism called "bridge-on-chip-amplification".

Cycle 3. Universal primers pU1 and pU2 anneal to the 3'-ends of immobilized extended reverse and forward primers (FIG. 2(A)). This is the first time in the reaction, when universal primers pU1 and pU2 are involved in the amplification process and direct the synthesis of nascent DNA strands. Forward and reverse complex primers, which were extended in Cycle 2, contain sequences CU2 and CU1 (complementary to U2 and U1) on their 3' ends, respectively. Universal primers pU1 and pU2 can now anneal to these sequences and direct synthesis of nascent DNA strands. These single stranded DNA fragments represent amplification products A and B flanked on both ends either by U2 and CU1, or U1 and CU2 and named as "modified target". The nascent DNA strands are not immobilized to the surface but temporarily bound to the complementary DNA strands, and therefore can be de-attached from the surface by heat denaturation.

Cycle 4. In this cycle, amplification proceeds in both compartments—on the surface of the gel elements and in the free space of the chamber (FIG. 2(B)). Starting with cycle 4, multiple immobilized complex primers direct the reaction on the surface, and a single pair of unbound universal primers directs amplification in solution. After heat denaturation in the beginning of Cycle 4, newly synthesized in Cycle 3 DNA strands leave the gel pads and diffuse into the free space of the reaction chamber. These amplification products are flanked by CU1 and CU2 sequences on their 3'-ends, and therefore universal primers pU1 and pU2 can anneal to these sequences and direct the synthesis of the nascent strands. Resulting modified targets are flanked by universal segments U1/CU1 and U2/CU2. Because the different specific products are flanked by common sequences, only a single pair of primers is required for the amplification of different targets. This type of PCR was named "pseudo monoplex". Conventional PCR in solution is more efficient then the amplification on a surface, so in early stages of the reaction, most of the amplification activity occurs in the off-surface space of the chamber. Two vertical arrows depict this conjuncture (FIG. 2(B)).

Intermediate Cycles. By the midpoint in thermal cycling, the amount of soluble modified targets is significantly higher than that of the immobilized amplification products (FIG. 2(B)). Higher efficiency of PCR in solution than of that on the solid support results in higher amount of soluble products. At the same time, the concentration of universal primers decreases with time, and therefore the amplification in solution slows down. On the other hand, the increased concentration of the modified targets in the reaction chamber leads to an increased amount of annealing complexes between the modified targets and the immobilized complex primers on a support, and therefore results in an increased kinetics of the target amplification on the surface of the support.

Final Cycles. Modified targets serve as templates in the extension of immobilized primers in the final cycles (FIG. 2(C)). Because there still is significant amount of the DNA polymerase activity left in the reaction chamber, the most of the amplification activity occurs to the solid support in the late stages of the reaction. Modified targets anneal to immobilized complex primers and are used as templates for the nascent strand synthesis in the final cycles of the reaction. This annealing and amplification leads to a dramatic increase in the amount of immobilized amplification products on the surface of a solid support.

Hybridization. Immobilized extended primers are detected by hybridization of microarrays with internal labeled reporting probes (FIG. 2(C)). Internal probes specifically interact with the amplification products and not with the immobilized primers. Alternative methods of detection such as incorporation of labeled dNTPs into DNA strands during amplification, or PCR with labeled universal primers are also suitable.

3. Details of Molecular Interactions of Primers and Target DNA on the Surface of the Microarray and in the Reaction Chamber in the First Four Cycles of the On-Chip PCR.

Figure 3A:
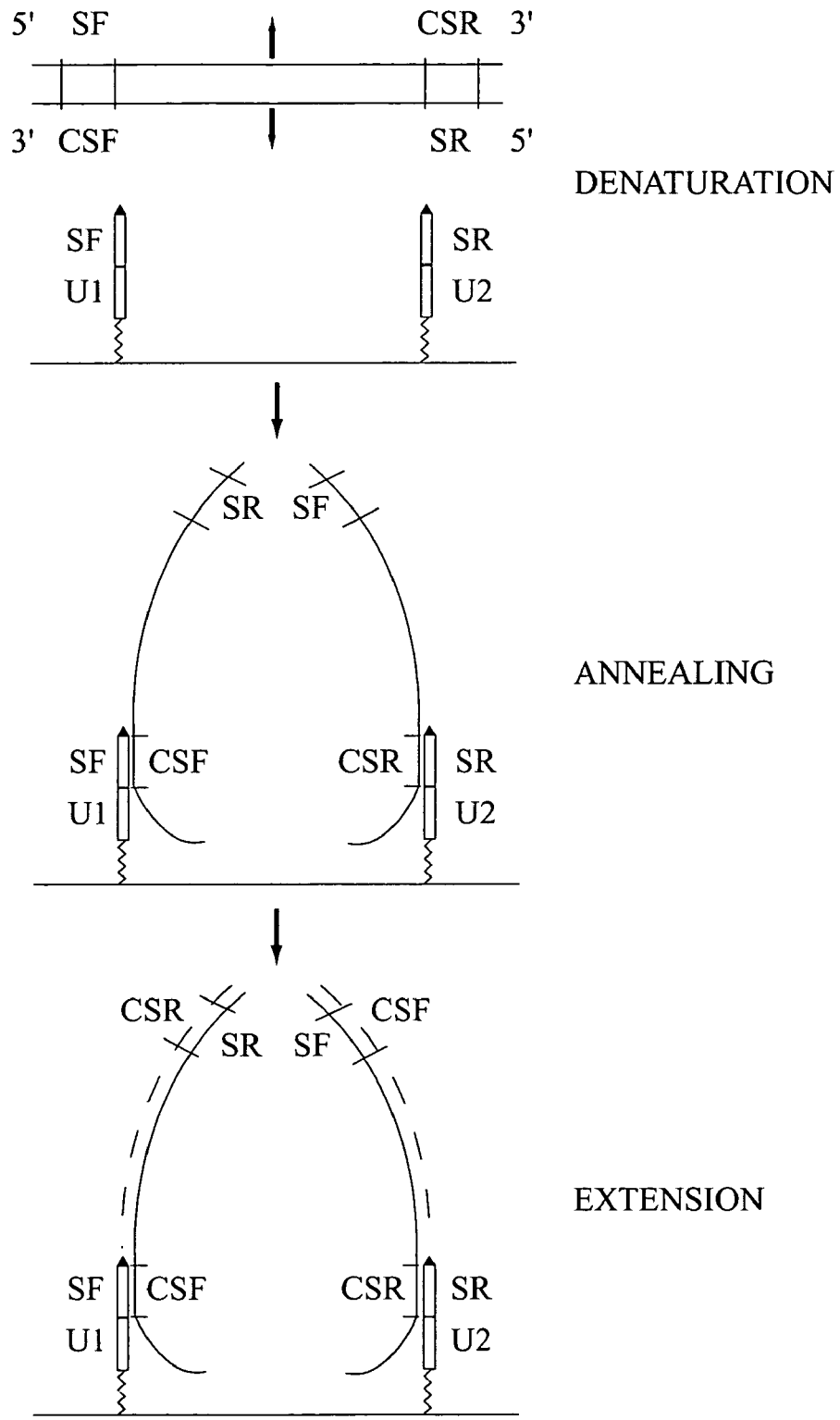
FIG. 3 shows a detailed schematic representation of molecular interactions during the first four cycles of dual-phase multiplex PCR.
Figure 3B:
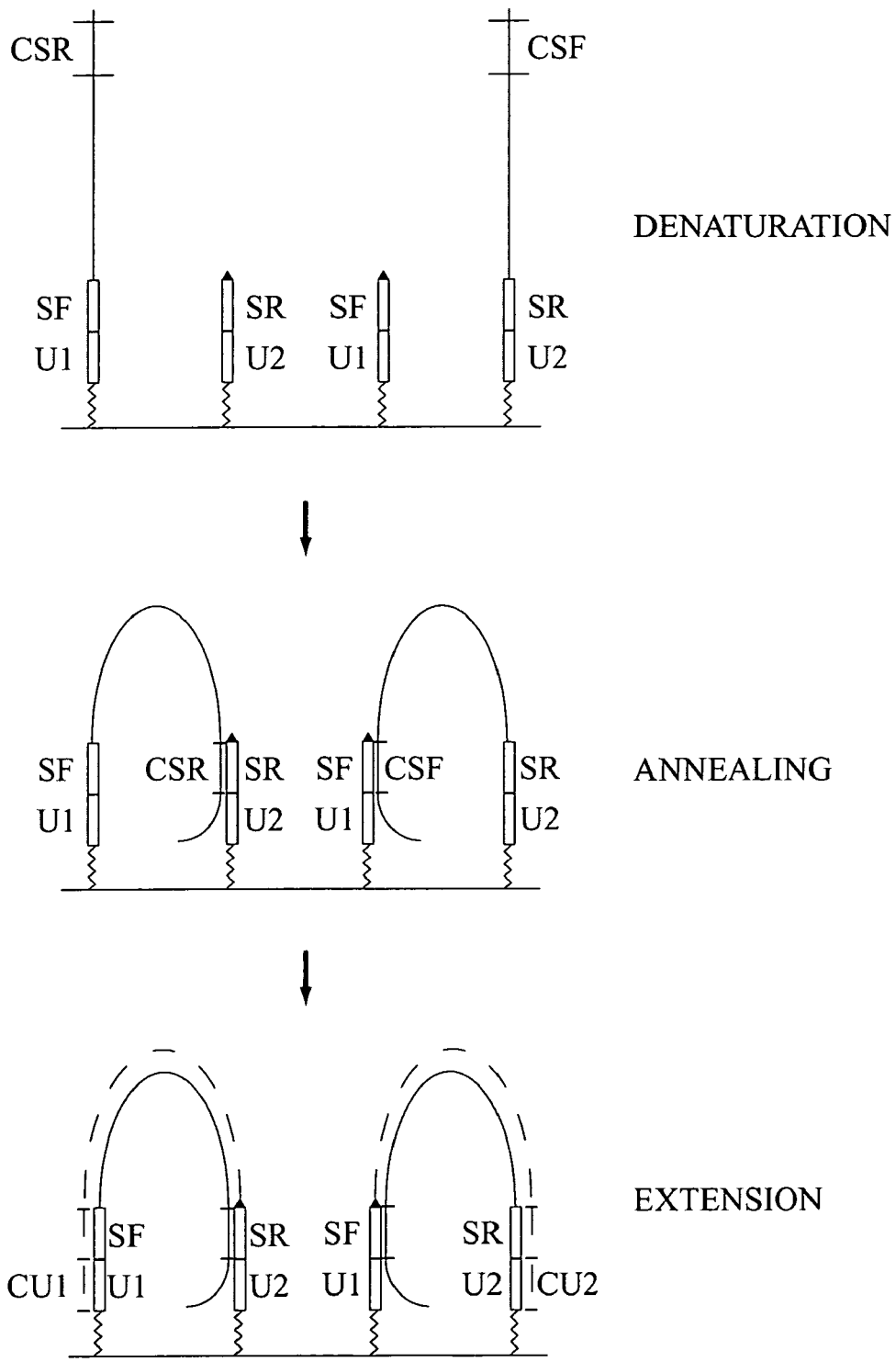
Figure 3C:
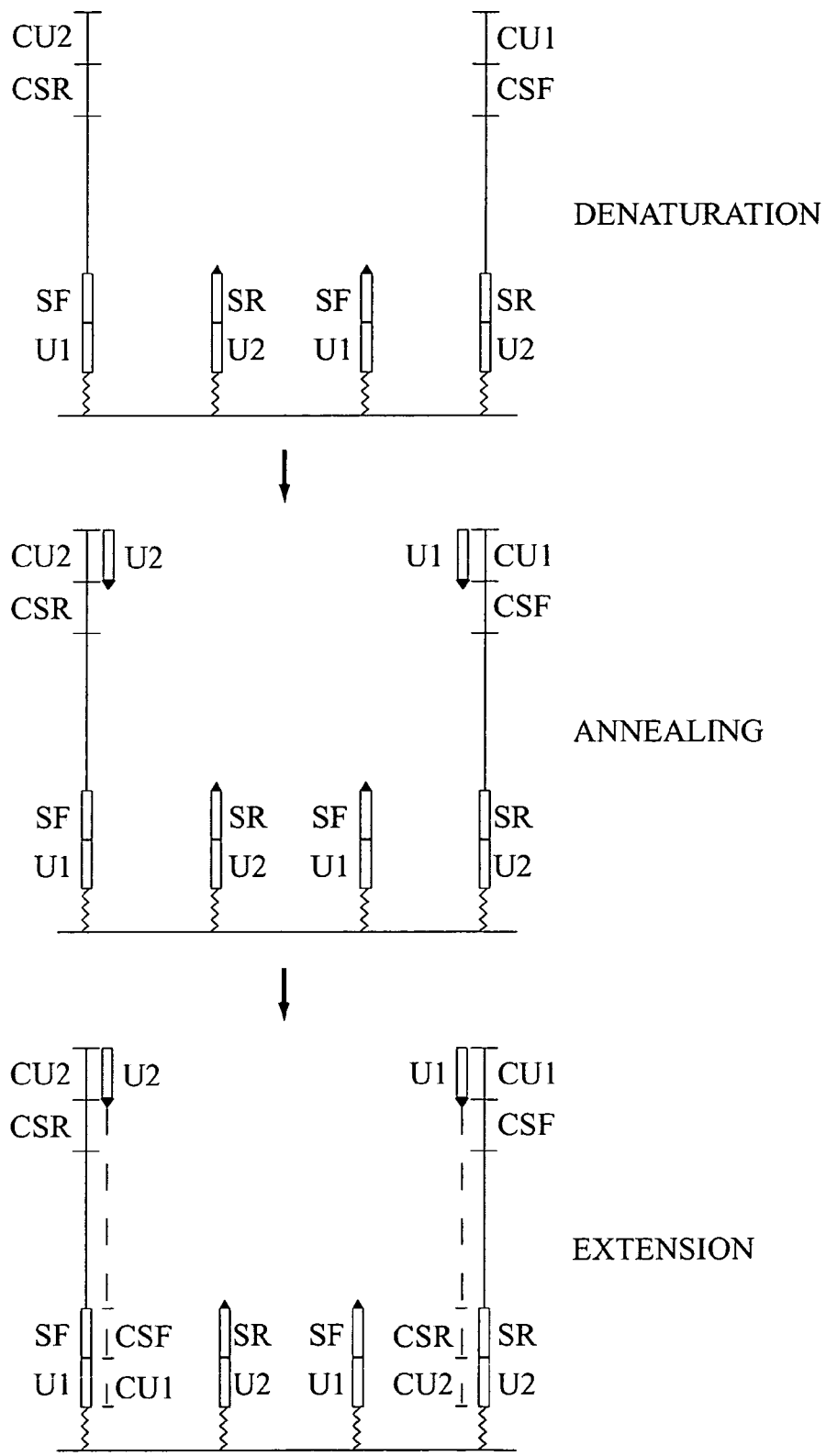

FIG. 3 shows a detailed schematic representation of molecular interactions during the first four cycles of on-chip multiplex PCR. The DNA denaturation, primer annealing and primer extension in four initial cycles are shown. As an illustration, only one DNA target and one gel element with immobilized complex primers are displayed.

(A) Cycle 1. The DNA denaturation, annealing of the target DNA to the immobilized primers and primer extension are illustrated. Strand separation of the double stranded target DNA in the denaturing step is depicted by two small vertical arrows pointed to opposite directions. Annealing events are illustrated by drawing the complementary sequences SF and CSF, and SR and CSR in close proximity of one to another. Primer extension events are denoted as dashed lines drawn in parallel to the solid lines that represent target DNA strands.

(B) Cycle 2. The denaturing of the reaction products; annealing of the immobilized extended primers to the immobilized primers that did not participate in the reaction in the first cycle; and primer extension are indicated.

(C) Cycle 3. The denaturing of the reaction products; annealing of the universal primers pU1 and pU2 to the immobilized extended primers; and the extension of the universal primers are displayed.

(D) Cycle 4. The denaturing of the reaction products; annealing of the universal primers pU1 and pU2 to the unattached modified targets of the reaction; and the extension of the universal primers are shown. Primers are represented by open rectangles with filled triangles at their 3'-OH ends. Parental DNA is shown as solid lines, nascent DNA is shown as dashed lines. Zigzagged lines represent linkers, through which the complex primers are attached to the gel pads. The unbound universal primers and the universal segments of the complex immobilized primers are called U1 and U2. Specific forward and specific reverse segments of complex primers are designated as "SF" and "SR", respectively. Sequences, which are complementary to SF, SR, U1 and U2, are denoted as CSF, CSR, CU1 and CU2, respectively.

4. Detection.

Identification of amplified DNA tethered to the solid support of microarray during or after amplification using incorporation of labeled nucleotides or during amplification with labels such as fluorescent dyes, luminescent dyes, or isotopes, or agents participating in immunological identification (such as avidin, biotin, and the like) can be performed.

When dual phase amplification is completed, PCR products on the gel pads are identified by hybridization of the biochip with any labeled probe that is complementary to the PCR products and not to the primers. Separation of amplified products is not necessary. The hybridization probes may be of two types: internal probes and end probes. Internal probes are sequence specific to each particular product, i.e. the number of internal probes is equal to the number of the products to be identified. Also, because all immobilized PCR products are flanked with CU1 and CU2 sequences at their 3'-ends, labeled U1 or U2 hybridization probes, can be used for that purpose. Using a single probe, either U1 or U2, will be sufficient to detect all products on the microarrays. This type of probe is designated as an end probe.

Alternatively, the PCR reaction can be performed with the universal primers pU1 and pU2, where one of the primers, or both are labeled at their 5'-ends. After PCR is completed, the biochip is washed and analyzed in a detection device (see Materials and Methods section). When hundreds of DNA targets are amplified and analyzed on a chip, the amount of time and costs saved on probe synthesis and labeling, as well as on multiple controls for the efficiency of hybridization with different probes, is significant.

Alternatively, the PCR reaction can be performed in the presence of fluorescently labeled precursors of DNA synthesis. This way, the fluorophores will be incorporated into the growing chains of the DNA products. After PCR is completed, the biochip is washed and analyzed in a detection device.

Alternatively, the products of the reaction can be analyzed by using molecular beacons. Molecular beacons are single-stranded oligonucleotide hybridization probes that form a stem-and-loop structure. The loop contains a probe sequence that is complementary to a PCR product sequence, and the stem is formed by the annealing of complementary arm sequences that are located on either side of the probe sequence. A fluorophore is covalently linked to the end of one arm and a quencher is covalently linked to the end of the other arm. A distinct molecular beacon is manufactured for each type of PCR products. The beacons are immobilized to the same gel elements that contain immobilized complex primers for amplification of the specific target. When there is little or no product on the gel pads, the beacons are in stem-and-loop conformation, which is unfavorable for the fluorescence. As the reaction goes on, the PCR products unfold the growing number of beacons being in the stem-and-loop conformation, thus causing the increasing intensity of fluorescence in the gel pads with each additional cycle.

Alternatively, identification of amplified DNA tethered to the solid support of microarray with labels can be performed during or after amplification using dyes that specifically interact with double stranded nucleic acids such as PicoGreen and Hoechst 33258 (Molecular Probes Inc., Eugene, Oreg.).

EXAMPLES

Example 1

PCR in Test Tubes with Complex and Universal Primers

Figure 4:
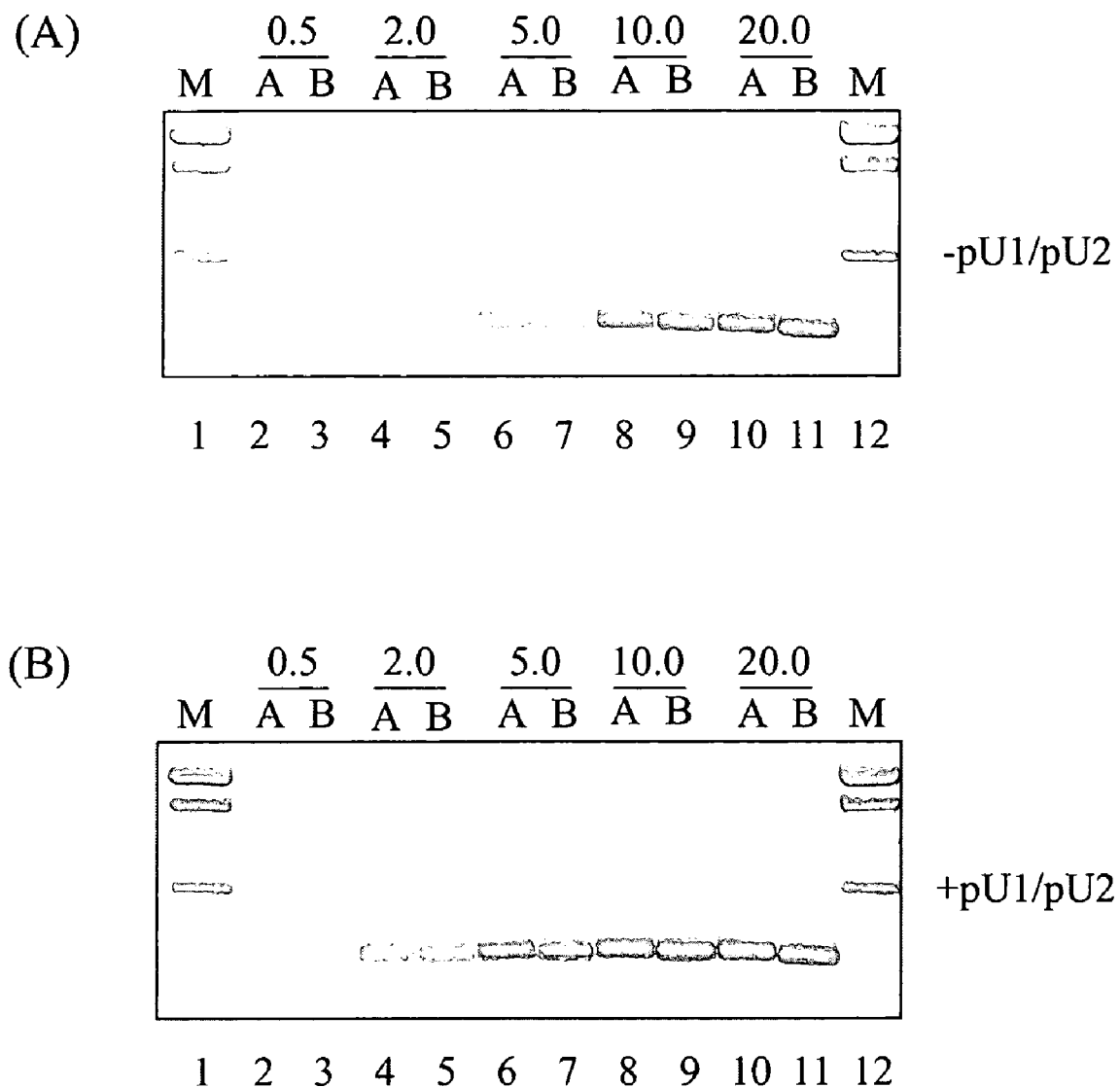
FIG. 4 illustrates a conventional PCR with complex and universal primers.

Ability of two types of primers, complex and universal, to support conventional PCR in tubes was tested. FIG. 4 illustrates a conventional PCR with complex and universal primers. Two pairs of complex primers, denoted A and B, and a single pair of universal primers, pU1 and pU2, were used in conventional PCR.

(A) Reaction without universal primers: Complex primers A and B were taken at increasing amounts: 0.5, 2.0, 5.0, 10.0 and 20.0 pmol of each per 25 µL of the reaction mix.

(B) Reaction with complex primers A and B, taken at concentrations as in FIG. 4(A), and pU1 and pU2 universal primers taken at concentration 20 pmol of each per 25 µL of the reaction mix is shown.

Lanes 2, 4, 6, 8 and 10 contain PCR products generated by primer pair A, and lanes 3, 5, 7, 9 and 11 contain PCR products generated by primer pair B. Lanes 1 and 12 with 100 bp DNA marker are denoted as M. Numbers above the lanes denote amounts of complex primers in pmol per reaction. The PCR reaction mixture contained either DNA target A (T-bm16S-723, see Table 1) and complex primers U1-Fa and U2-Ra at increasing concentrations from 0.5 pmol to 20 pmol of each primer per reaction (FIG. 4(A), lanes 2, 4, 6, 8 and 10) or DNA target B (T-bm16S-726, see Table 1) and corresponding to it complex primers U1-Fb and U2-Rb at different concentrations (FIG. 4(A), lanes 3, 5, 7, 9 and 11). After 30 cycles PCR was stopped and the reaction products were separated on 1% agarose gel. The expected sizes of PCR products in the reactions are 205 bp and 197 bp, respectively.

The yield of PCR greatly depends on the amount of primers in the reactions. The efficiency of the reactions shown on FIG. 4(A) drops tremendously when the amount of complex primers is below 5 pmol per reaction (compare lanes 2-5 to lanes 6-11 on FIG. 4(A)). In contrast, when the same reactions were supplied with a pair of universal primers pU1 and pU2 at concentrations of 20 pmol of each per 25 µL of the reaction mix (FIG. 4(B)), the amount of products significantly increased in all reactions, being most visible in the first four reactions (compare lanes 2-5 on FIG. 4(A) with lanes 2-5 on FIG. 4(B)). When used alone without complex primers, universal primers pU1 and pU2, did not yield any PCR products. Thus, universal primers pU1 and pU2 and complex specific primers work synergistically, which leads to significantly increased yield of the PCR products.

Example 2

Dual-Phase PCR Proceeds through the Formation of Modified Targets

Figure 5:
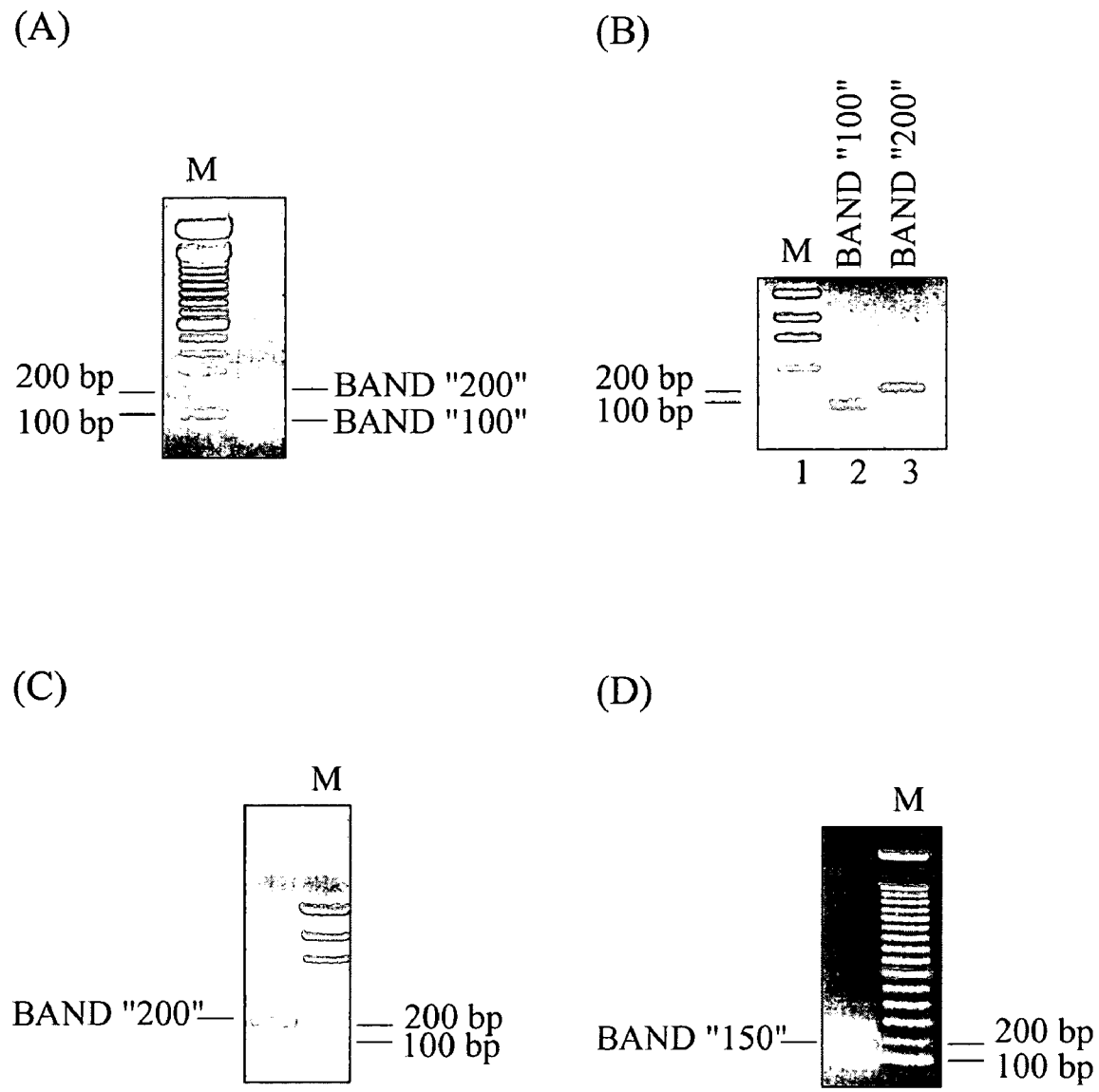
FIG. 5 illustrates dual-phase PCR reaction through synthesis of modified targets.

To demonstrate the presence of modified targets in the reaction mix upon the completion of the reaction content of PCR mixture in the reaction chamber was analyzed. FIG. 5 illustrates that dual-phase PCR reaction proceeds through synthesis of modified targets.

(A) Microarrays were manufactured by immobilizing complex primers U1-Fa and U2-Ra (see Table 1) to a standard array of gel pads. A suitable support such as a 2-dimensional (2D) surface or a 3-dimensional (3D) matrix, including glass slides, microbeads, microcanals, gel pads, membranes, metal, plastic and any suitable matrix can be used in the fabrication of microarrays. On the chromosomal map of *Bacillus mycoides*, the distance between the 5'ends of the specific segments of the complex primers -Fa and -Ra was 165 bp, the combined length of the universal segments -U1 and -U2 is 40 bp, and therefore, the calculated size of the modified target in this experiment would be 205 bp. The on-chip amplification reactions were supplied with a pair of universal primers pU1 and pU2 and with $10^6$ copies of target DNA "T-bm16S-723"- a 723 bp-long PCR fragment, residing in the 5-half of the 16S rRNA gene of *B. mycoides*. PCR was carried out for 30 cycles, the reaction mix was collected, and an aliquot was analyzed on 1.2% agarose, along with 100 bp DNA marker (M). Band "200" and Band "100" are two major products of the PCR reaction occurring in the off-surface space of the reaction chamber.

(B) To demonstrate the nature of the two major products shown on FIG. 5(A), the rest of the sample was re-amplified in a conventional PCR reaction, using universal primers pU1 and pU2, and separated on 1.2% agarose gel electrophoresis. The bands "200" and "100" were cut out of the gel, and the DNA fragments were extracted from the agarose. After ethanol precipitation, the samples were analyzed on 1.2% agarose gel, along with a low-mass DNA ladder (M). After gel purification of the 100 bp and the 200 bp fragments, the samples were sent for DNA sequencing. The sequencing analysis of the "200 bp" product revealed that its internal part had a nucleotide sequence identical to the 165 bp fragment enclosed between the 5'ends of specific segments -Fa and -Ra, and that this internal part is flanked on both sides by U1 and U2 sequences. Sequencing of the "100 bp" product produced mixed results, which is due to the possibility that the product represents a mixture of primer dimers.

(C) The experiment described in FIG. 5(A) was repeated, except that the reaction was carried out for 45 cycles. The sample was separated on 1.2% agarose gel, along with a low-mass DNA ladder (M). The repetition of PCR reaction represented on FIG. 5(A) for 45 cycles again revealed 100 bp and 200 bp bands. However, the yield of the modified target band "200", was much higher.

(D) To demonstrate that the synthesis of modified targets is independent of the nucleotide sequences of the primers used in the reaction, the experiment described in FIG. 5(C) was repeated, except that a different pair of complex primers, U5-Fc and U6-Rc, was immobilized to the microarrays, and different universal primers, pU5 and pU6, were used in the reaction. The reaction mix was analyzed on 1.2% agarose, along with a 100 bp DNA ladder. The calculated size of the modified target in these experiments was 150 bp, which was in perfect agreement with the experimental data. The modified targets were synthesized only in those reactions that were carried out in the presence of the universal primers. Exclusion of the universal primers from the reaction mixes completely prevented the synthesis of the modified targets.

Example 3

Universal Primers Dramatically Increase Efficiency of On-Chip PCR

Addition of the universal primers into the reaction mix affects the efficiency of the on-chip PCR. The absence of universal primers in the reaction mix prevents the synthesis of modified products, and therefore, affects the yield of the PCR.

Figure 6:
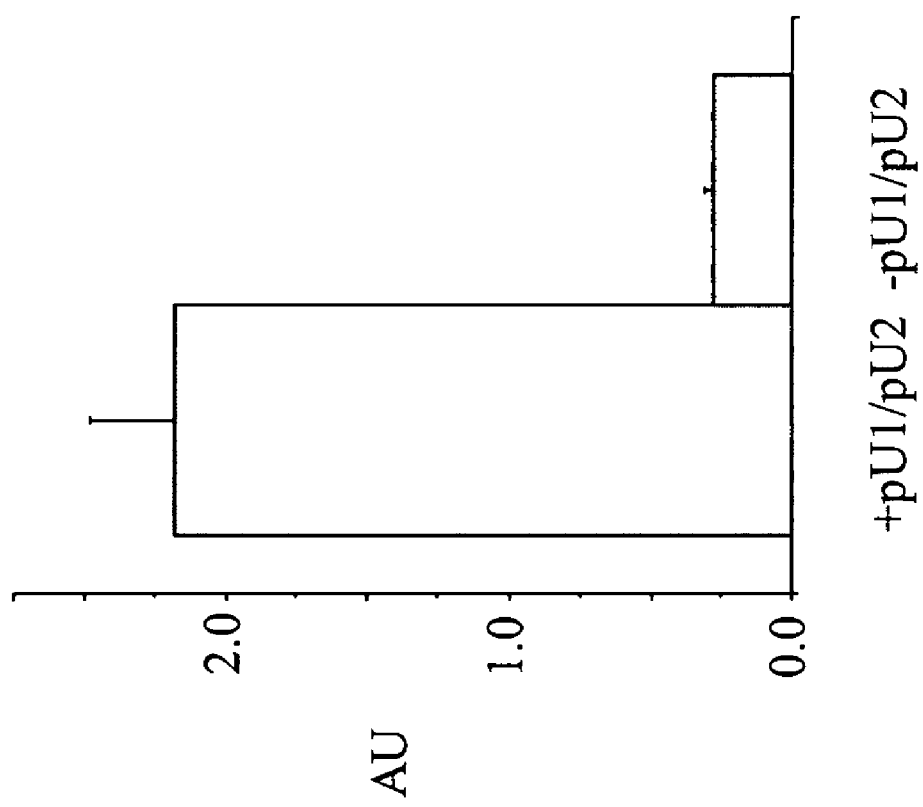
FIG. 6 illustrates dual-phase PCR with or without universal primers.

FIG. 6 illustrates on-chip PCR with or without universal primers. Microarrays were manufactured by immobilizing complex primers U1-Fa and U2-Ra (see Table 1) to a standard array of gel pads. PCR on microarrays was performed either with or without the addition of universal primers pU1 and pU2 into a reaction mix. After PCR, the microarrays were hybridized with a reporting probe labeled with a fluorescent dye. In addition to various fluorescent dyes, a reporting probe can be labeled with all suitable detecting compounds such as radioactive isotopes, gold particles, light scattering particles, energy transferring compounds, luminescent dyes, ligands such as biotin, etc. After hybridization, images were acquired, quantified and the intensities of fluorescent signals were plotted as a bar graph. AU stands for arbitrary units. The ratio between the signals generated on microarrays in the reactions, which were run in the presence of universal primers, to those generated in reactions where universal primers were omitted ranged from 5.19 to 10.46, giving an average value of 8.40±1.05. Thus, addition of the universal primers into the reaction mix led to 5-10 fold increase in the end-point amounts of the amplification products.

Example 4

Type of Target DNA Does Not Have a Major Effect on the On-Chip PCR

Figure 7:
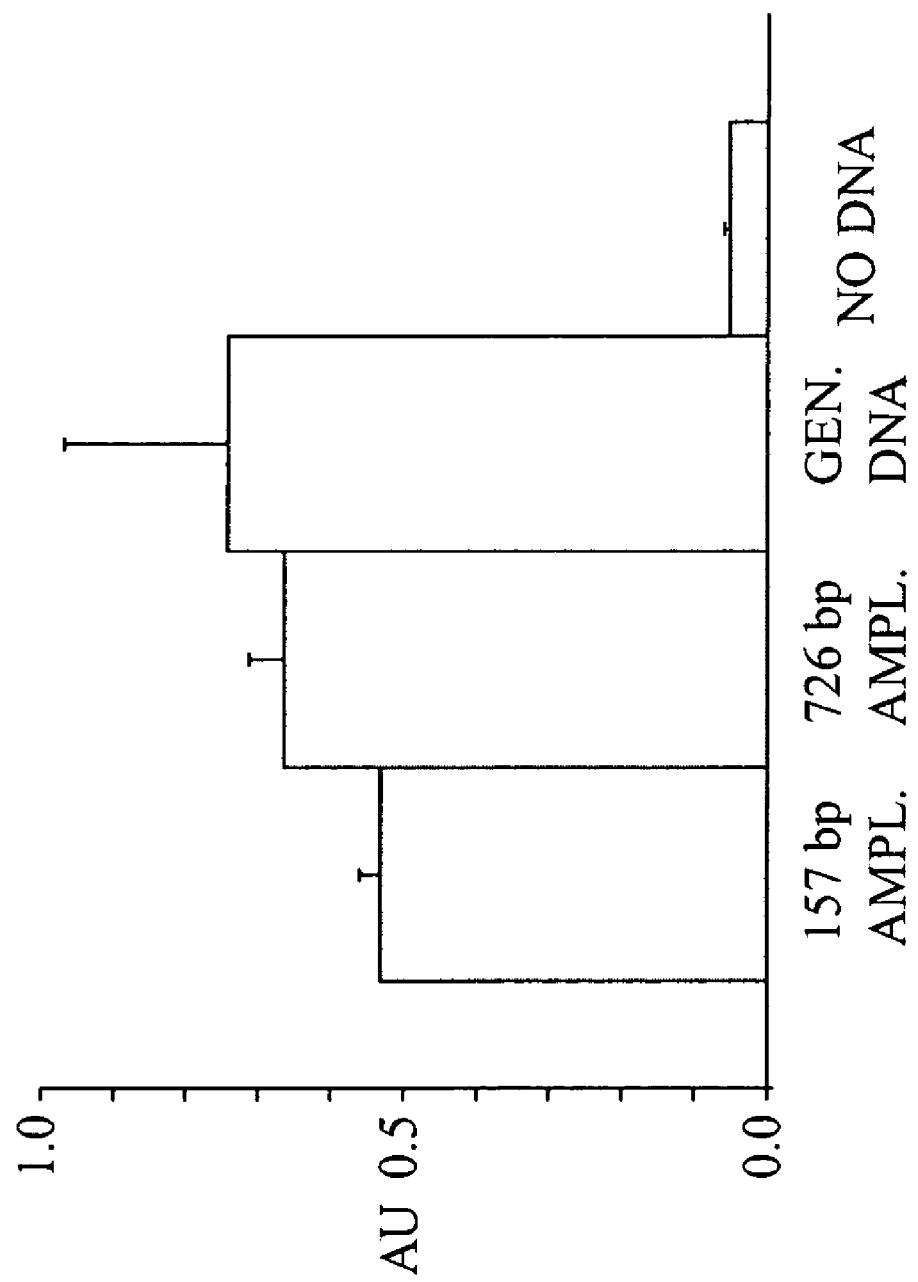
FIG. 7 illustrates dual-phase PCR with target DNA of varying complexity and size.

The complexity of the DNA sample and the size of the target have no effect on the amount of the amplification products. FIG. 7 illustrates on-chip PCR with target DNA of varying complexity and size. The end-point yields of the amplification products in on-chip reactions were compared in FIG. 7. The reactions were carried out with either genomic DNA of *B. mycoides*, or with PCR generated DNA fragments called amplicons. Prior to PCR, the genomic DNA was treated with DNase I to decrease the average size of the fragments to approximately 800 bp. Two DNA fragments, 157 bp and 726 bp long (see Table 1, targets T-bm16S-157 and T-bm16S-726, respectively), were generated by PCR in test tubes. On the chromosomal map of *B. mycoides*, 157 bp fragment resides inside 726 bp fragment, and both fragments are localized in the 3'half of the 16S rRNA gene.

Microarrays were manufactured by immobilizing complex primers U5-Fc and U6-Rc (see Table 1) to a standard array of gel pads. Specific segments of the primers, -Fc and -Rc, are identical to the primers used for the synthesis of the 110 bp fragment. This way, the same 110 bp product would be generated in the reactions with each of these templates. In amplification reactions in test tubes with primer pair pFc and pRc, each of the above-mentioned templates produced approximately the same amount of the 110 bp product as was analyzed by the ethydium bromide staining of the products in agarose gel. The amplification reactions were supplied with a pair of universal primers pU5 and pU6, and either $10^6$ copies of 157 bp amplicon, $10^6$ copies of 726 bp amplicon, an amount of *B. mycoides* genomic DNA equivalent to $10^6$ genomes of the bacteria, or no DNA.

Four separate on-chip PCR amplifications, adding to the reaction mix a pair of universal primers pU5/pU6 and either $10^6$ copies of 157 bp amplicon, or $10^6$ copies of 726 bp amplicon, or 4.5 ng of *B. mycoides* genomic DNA (the amount equivalent to $10^6$ genomes of the bacteria) or no DNA were performed. After 50 cycles of PCR, the microarrays were hybridized with a reporting probe bm16S-IP3'h.

All three templates produced a robust signal on the gel pads occupied by the primers, whereas virtually no signals were observed in the reactions where DNA templates were omitted from the reaction mix. Quantitative analysis of the images revealed that each type of the templates supported on-chip PCR to approximately the same end-point signal intensities. The labels below the bars indicate the target used in the reaction. AU—arbitrary units. The observed differences between the signals are not statistically significant.

Thus, as in the PCR in test tubes, neither the size of the targets nor the complexity of the DNA samples seems to have a major effect on the efficiency of the on-chip amplification.

Example 5

Multiple Targets can be Amplified Simultaneously in a Single On-Chip PCR Reaction To demonstrate the possibility of simultaneous amplification of multiple DNA targets in a single on-chip PCR reaction six pairs of complex primers for amplification of fragments, ranging from 110 bp to 150 bp, which reside in six functional genes of *Bacillus subtilis*: dnaK, ebrA, fruR, grpe, spo0A, and yisY (see Table 1) were designed.

Figure 8:
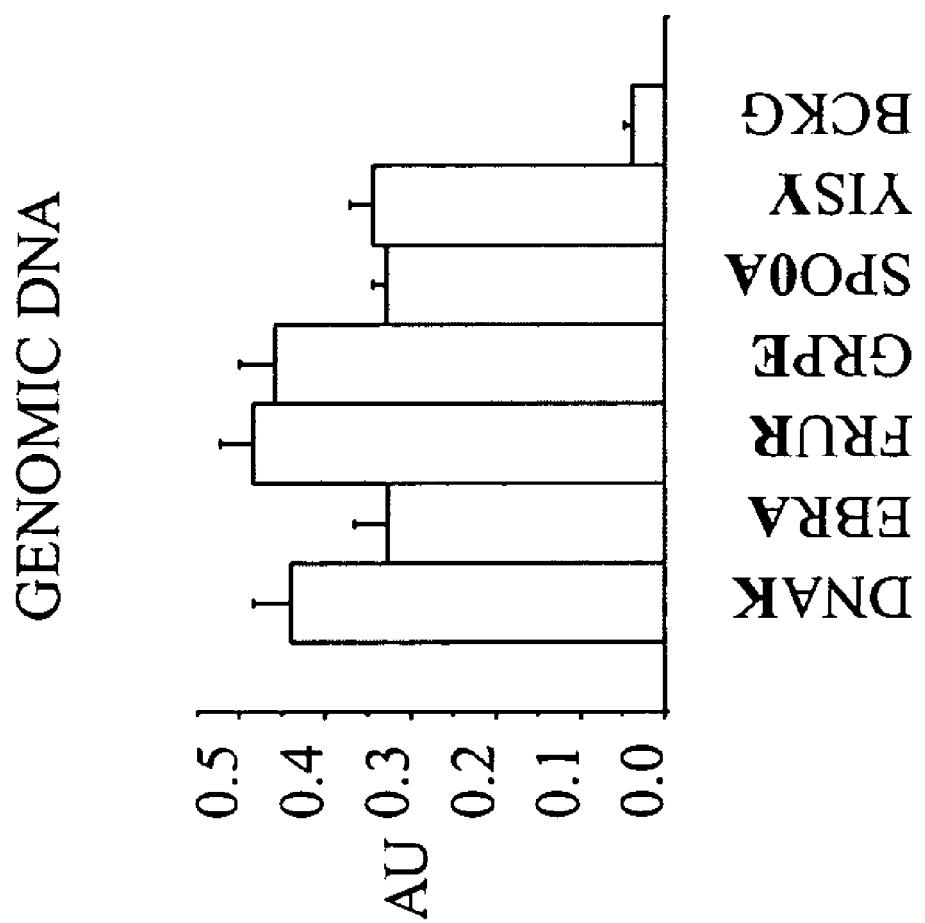
FIG. 8 shows the results of a multiplex dual-phase PCR.

FIG. 8. shows the results of a multiplex on-chip PCR. For the multiplex on-chip amplifications, a reaction system based on using the Self Seal Reagent™ (MJ Research Inc., Waltham, Mass.) that seals reaction chamber and improves signal/background ratio was utilized. Microarrays were manufactured by immobilizing six different pairs of complex primers, designed for the amplification of six different functional genes of *B. subtilis*: dnaK, ebrA, fruR, grpE, spo0A, and yisY (See Material and Methods and Table 1 for the primer list) to the gel elements. The reaction mix was supplied with a pair of universal primers pU5 and pU6 and 4.5 ng of *B. subtilis* genomic DNA, the amount equivalent to $10^6$ copies of the bacterial genome. After PCR, the microarrays were hybridized with a mixture of six reporting probes, bsDnaK2, bsEbrA1, bsFruR2, bsGrpE2, bsSpo0A1, and bsYisY2, each capable of recognizing one of the six products. Images were quantified, and the data were plotted as a bar graph. All six pairs of primers supported amplification to a very similar extent, and corrected for the background signals, were seven to twelve times above the background. Signals were not detected on the primer-loaded gel elements in reactions where genomic DNA was omitted.

Thus, six targets present in genomic DNA sample were simultaneously amplified in a single reaction.

Example 6

Multiplex On-Chip PCR is Highly Specific

The experiment described in FIG. 8 was repeated, except that the genomic DNA was replaced with $10^6$ copies of one of the six amplicons—T-bsDnaK, T-bsEbrA, T-bsFruR, T-bsGrpE, T-bsSpo0A, or T-bsYisY (Table 1). Six pairs of complex primers for amplification of fragments that ranged from 110 bp to 150 bp, which reside in six functional genes of *Bacillus subtilis*: dnaK, ebrA, fruR, grpE, spo0A, and yisY (see Table 1) were designed to demonstrate specificity of multiplex on-chip amplification. FIG. 9 shows that multiplex on-chip PCR is highly specific (A-F). All six pairs of primers to the gel elements on the same biochip were immobilized. Each pair of primers was spotted on a cluster of ten adjacent gel elements, so that there were 60 loaded gel pads on each microarray. As targets for the PCR reactions, we used $10^6$ copies of PCR-generated fragments—amplicons—specific to one of the six pairs of primers immobilized to the biochips (Table 1).

After PCR, the microarrays were hybridized with a set of six reporting probes: bsDnaK2, bsEbrA1, bsFruR2, bsGrpE2, bsSpo0A1, and bsYisY2, each capable of recognizing one of the six PCR products. Labels above the panels show the name of the target—one of the six amplicons. Labels below each bar in the bar graphs represent the name of the complex primers immobilized to the gel pads. "bckg" denotes background. Each of the six panels labeled (A) through (F) represents results from one of the six on-chip PCR amplifications carried out with one of the six amplicons.

Analysis of the data revealed that amplification occurred only on those pads that were loaded with the primers corresponding to the specific amplicon added into the reaction mix. No amplification took place on the pads loaded with other primers (FIG. 9(A-F)). In one case, where ebrA amplicon was used as a target, the signals on the pads loaded with dnaK primers were higher than the background (FIG. 9(B)). This may be due to slight cross-reactivity of the ebrA amplicons with the immobilized dnaK primers. Nevertheless, it was the only false positive out of 36 possible outcomes, and there were no false negatives in this experiment. The efficiency of amplification of the targets in monoplex on-chip reactions was approximately the same as the efficiency of amplification of the targets in the multiplex PCR (compare FIG. 9 and FIG. 8).

Example 7

Detection Limit of the Multiplex On-Chip PCR

Figure 10A:
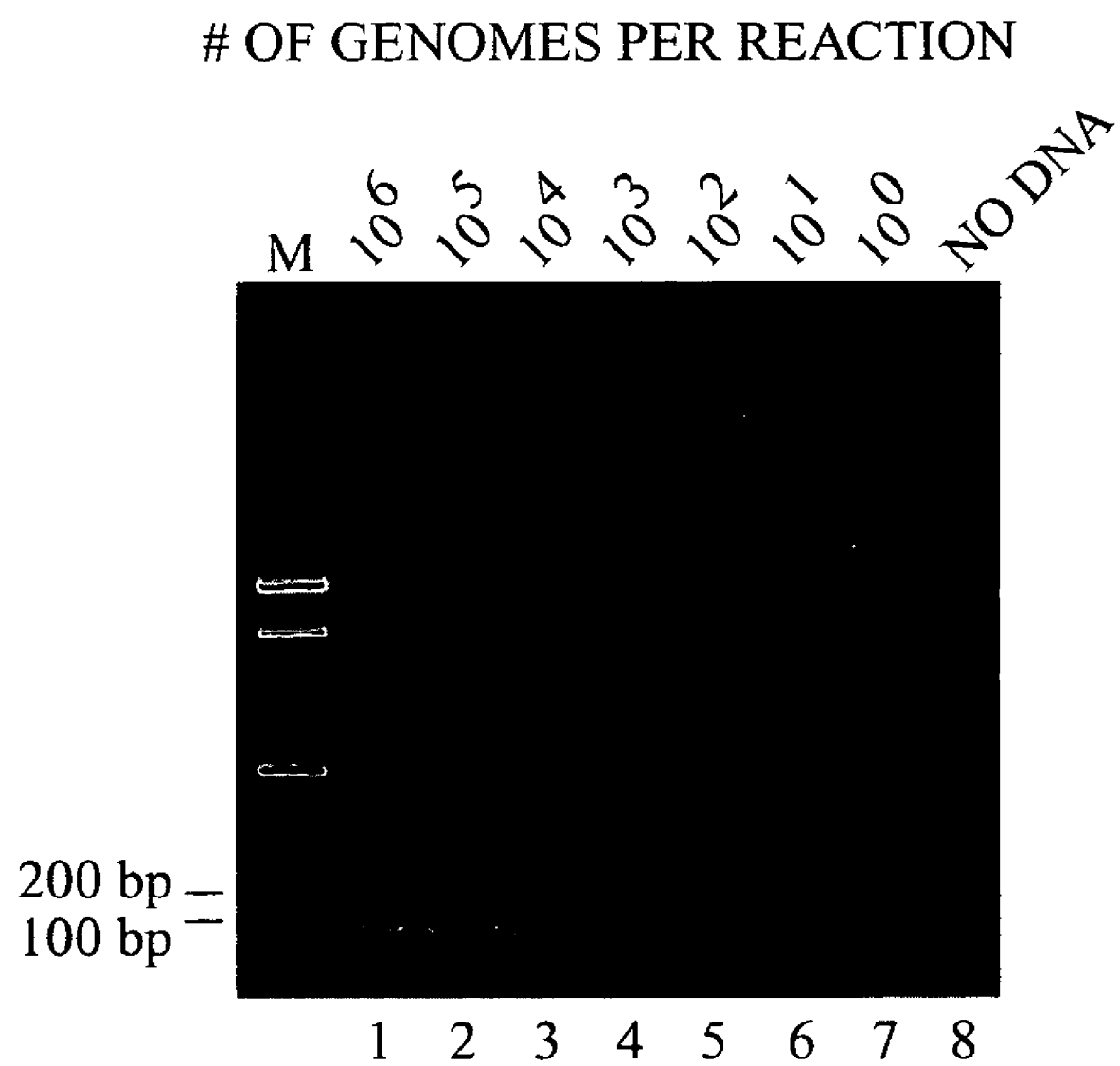
FIG. 10 shows the detection limit of dual-phase PCR.
Figure 10B:
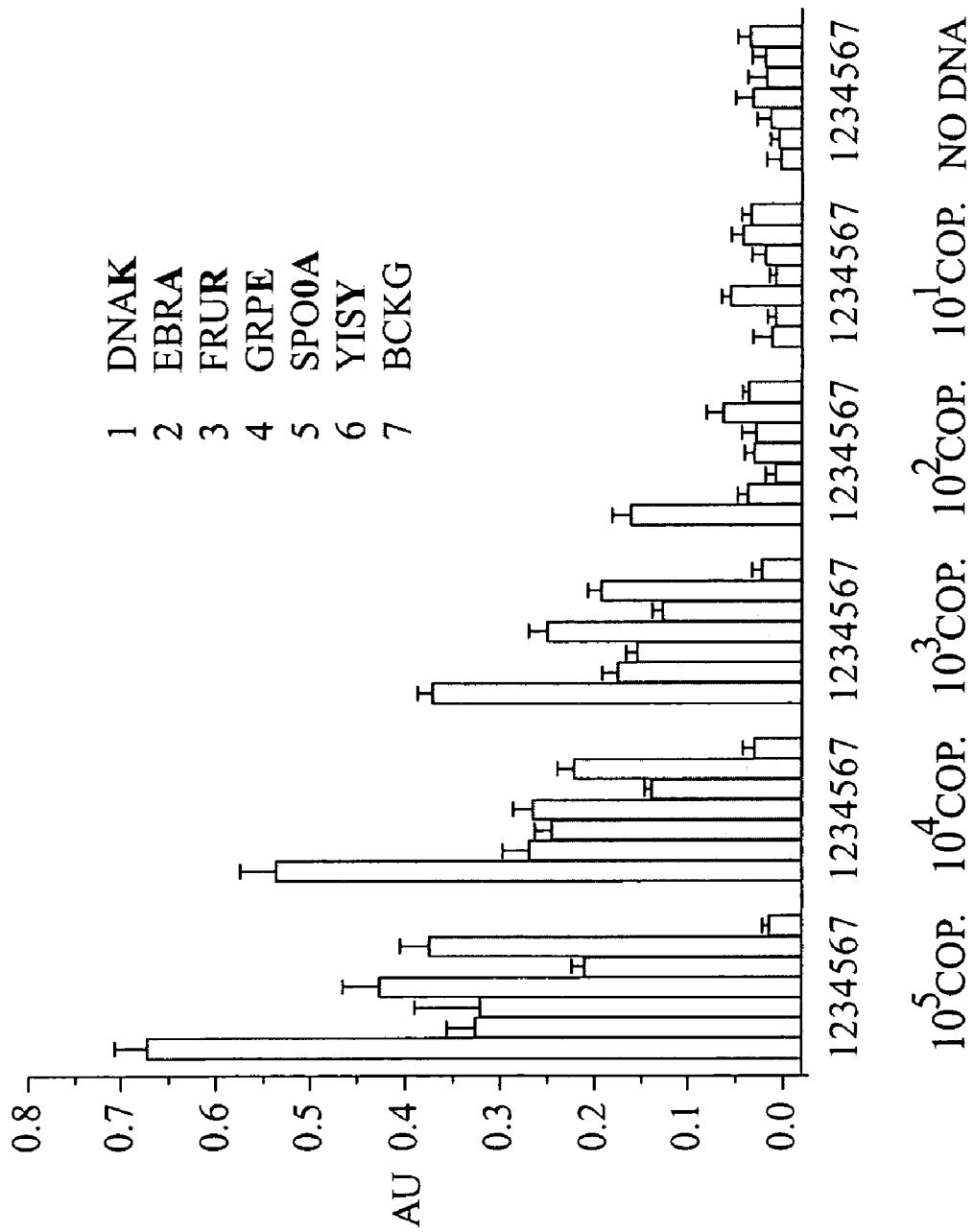

FIG. 10 shows the detection limit of on-chip PCR. (A) PCR amplifications were conducted in test tubes with decreasing amounts of the genomic DNA. Serial dilutions of total genomic DNA of *B. subtilis* at concentrations of $10^6$, $10^5$, $10^4$, $10^3$, $10^2$, $10^1$, and $10^0$ genomes per μL were prepared. Seven separate conventional PCR reactions containing primers pGrpE-F/pGrpE-R (Table 1) and decreasing amounts of the genomic DNA and were run for 50 cycles. An additional mock reaction with no DNA added was performed. The products of the reactions were separated on 1.2% agarose gel. The labels above the lanes denote the amount of *B. subtilis* genomic DNA used in the reaction, expressed in equivalents of the bacterial genomes. "NO DNA" lane contains the product of mock PCR reaction, performed without addition of DNA. M–100 bp DNA ladder. The results are shown on FIG. 10(A). The amount of the 126 bp product of the reaction dropped significantly when the number of copies of the input DNA was lowered below 100 copies per reaction (FIG. 10(A) compare lanes 1-5 and 6-8).

(B) Microarrays, identical to those used in the experiment shown in FIG. 8, were used for multiplex PCR with different amounts of *B. subtilis* genomic DNA. Six independent on-chip PCR reactions were performed with either $10^5$, $10^4$, $10^3$, $10^2$, $10^1$ copies of *B. subtilis* genomes, or with no DNA added. After PCR, the microarrays were hybridized with a *B. subtilis* set of six reporting probes that was used in the experiment, which data is shown on FIG. 8.

The images were quantified, and the data was presented as bar graphs. The labels below each bar in the bar graph panels denote the name of complex primers, immobilized to the corresponding gel elements. Labels below each bar graph panel denote the amount of the bacterial genomic DNA, expressed in the number of copies of the bacterial genome. In the reactions, supplied with $10^5$, $10^4$ and $10^3$ copies of the bacterial genomes, robust signals were produced on all gel pads occupied by the immobilized complex primers. The signals on the gel pads occupied with complex DNAK primers were above the background even in the experiment when only 100 copies of the genomic DNA were added in the reaction (FIG. 10(B)). Thus, $4.5 \times 10^{-12}$ g of *B. subtilis* DNA, which is equivalent to 1,000 genomes of the bacteria, could be easily detected using the described approach. Through rigorous primer selection, a smaller amount of bacterial genomic DNA (equivalent to 100 genomes) can be sensed by this approach.

Example 8

Multiplex PCR on a Planar Support

The multiplex reaction that involves immobilized complex primers and universal primers is also performed on planar supports such as a glass slide. Plain or modified glass slides are imprinted with complex primers. Multiplex amplification through bridge formation is performed with complex and universal primers. The psuedo-monoplex amplification is performed with universal primers in the liquid phase of a reaction chamber. The modified targets (amplified target nucleic acid molecules that have a specific internal fragment and common universal sequences at the end) increase the annealing and the amplification in the surface of the planar support. Detection of amplified target nucleic acids can be performed through hybridization of labeled probes or through incorporation of labeled nucleotides during the amplification process or by end-labeling the complex primers.

Table 1: Designation and sequences of oligonucleotides (SEO ID NOS 1-54, respectively, in order of appearance)

TABLE 1

Designation and sequences of oligonucleotides (SEQ ID NOS 1-54, respectively, in order of appearance)

| Oligo ID[a] | Function[b] | Sequence[c] |
|---|---|---|
| U1-Fa | Cmplx prmr | gctaaatcggactagctacccacactgggactgagacac |
| U2-Ra | Cmplx prmr | taatccagctacgctgcatcgccagcttattcaactagcac |
| U1-Fb | Cmplx prmr | gctaaatcggactagctacctcatcatgccccttatgacc |
| U2-Rb | Cmplx prmr | taatccagctacgctgcatccgcgattactagcgattcc |
| U1-Fc | Cmplx prmr | ggattaggtgagattgaggtacaaagagctgcaagacc |
| U2-Rc | Cmplx prmr | taatccagctacgctgcatccgcgattactagcgattcc |
| U5-Fc | Cmplx prmr | ttttcttctctcccaatctcgtacaaagagctgcaagacc |
| U6-Rc | Cmplx prmr | atcagcaatgccttctaagtccgcgattactagcgattcc |
| U5-dnaK-F | Cmplx prmr | ttttcttctctcccaatctcgcttccagcttactgatatcc |
| U6-dnaK-R | Cmplx prmr | atcagcaatgccttctaagtcgttttgttcttttcctgtgcc |
| U5-ebrA-F | Cmplx prmr | ttttcttctctcccaatctcaaccatattcccctgagcc |
| U6-ebrA-R | Cmplx prmr | atcagcaatgccttctaagtcagtaacacgaccctgatag |
| U5-fruR-F | Cmplx prmr | ttttcttctctcccaatctccgatcaaacaggcaaaacac |
| U6-fruR-R | Cmplx prmr | atcagcaatgccttctaagtcaatgtaagctcttcagcgtc |
| U5-grpE-F | Cmplx prmr | ttttcttctctcccaatctcgaagccgacaatgaacagac |
| U6-grpE-R | Cmplx prmr | atcagcaatgccttctaagtcaggatcaaattcctgccctac |
| U5-spo0A-F | Cmplx prmr | ttttcttctctcccaatctcaggacaggaagacatggaag |
| U6-spo0A-R | Cmplx prmr | atcagcaatgccttctaagtctccctcagcctctctaaaac |
| U5-yisY-F | Cmplx prmr | ttttcttctctcccaatctcgccgatgatgtgaaagcag |
| U6-yisY-R | Cmplx prmr | atcagcaatgccttctaagtcgccgcagacagtaaaatcag |
| pU1 | Unvrsl prmr | gctaaatcggactagctacc |
| pU2 | Unvrsl prmr | taatccagctacgctgcatc |
| pU5/AP000522/12788-12808 | Unvrsl prmr | ttttcttctctcccaatctc |
| pU6/AP000522/14015-13995 | Unvrsl prmr | atcagcaatgccttctaagtc |
| pFa/AF155957/310-329 | Spcfc prmr | cacactgggactgagacac |
| pRa/AF155957/474-453 | Spcfc prmr | gccagcttattcaactagcac |
| pFb/AF155957/1198-1218 | Spcfc prmr | tcatcatgccccttatgacc |

TABLE 1-continued

Designation and sequences of oligonucleotides
(SEQ ID NOS 1-54, respectively, in
order of appearance)

| Oligo ID[a] | Function[b] | Sequence[c] |
| --- | --- | --- |
| pRb/AF155957/1354-1335 | Spcfc prmr | cgcgattactagcgattcc |
| pFc/AF155957/1245-1264 | Spcfc prmr | gtacaaagagctgcaagacc |
| pRc/AF155957/1354-1335 | Spcfc prmr | cgcgattactagcgattcc |
| pFd/AF155957/38-56 | Spcfc prmr | gcctaatacatgcaagtcgag |
| pRd/AF155957/758-738 | Spcfc prmr | tcagtgtcagttacagaccag |
| pFe/AF155957/770-790 | Spcfc prmr | gtggggagcaaacaggattag |
| pRe/AF155957/1495-1475 | Spcfc prmr | acttcaccccaatcatctgtc |
| pDnaK-F/Z99117/12237-12217 | Spcfc prmr | gcttccagcttactgatatcc |
| pDnaK-R/Z99117/12110-12130 | Spcfc prmr | gttttgttcttttcctgtgcc |
| pEbrA-F/Z99113/57310-57292 | Spcfc prmr | aaccatattcccctgagcc |
| pEbrA-R/Z99113/57162-57181 | Spcfc prmr | agtaacacgacccctgatag |
| pFruR-F/Z99111/96526-96545 | Spcfc prmr | cgatcaaacaggcaaaacac |
| pFruR-R/Z99111/96652-96633 | Spcfc prmr | aatgtaagctcttcagcgtc |
| pGrpE-F/Z99117/13794-13775 | Spcfc prmr | gaagccgacaatgaacagac |
| pGrpE-R/Z99117/13669-13698 | Spcfc prmr | aggatcaaattcctgccctac |
| pSpo0A-F/Z99116/108839-108820 | Spcfc prmr | aggacaggaagacatggaag |
| pSpo0A-R/Z99116/108693-108712 | Spcfc prmr | tccctcagcctctctaaaac |
| pYisY-F/Z99109/157532-157550 | Spcfc prmr | gccgatgatgtgaaagcag |
| pYisY-R/Z99109/157677-157658 | Spcfc prmr | gccgcagacagtaaaatcag |
| bm16S-IP5'h/AF155957/371-390 | Probe | aatggacgaaagtctgacgg |
| bm16S-IP3'h/AF155957/1301-1320 | Probe | tcggattgtaggctgcaact |
| bsDnaK2/Z99117/12141-12161 | Probe | gctcttacgtttacgataccg |
| bsEbrA1/Z99113/57190-57209 | Probe | gaatcccgataagccctttg |
| bsFruR2/z99111/96549-96568 | Probe | tacgtcttagcagacccttc |
| bsGrpE2/Z99117/13718-13737 | Probe | ttcaaggcttctacgagctg |
| bsSpo0A1/Z99116/108795-108814 | Probe | tgtccgttataagcaacgcc |
| bsYisY2/Z99109/157602-157583 | Probe | cccattgaaaaaccggcaag |
| T-bm16S-723/AF155957/36-758 | Target | 723 bp PCR amplicon |
| T-bm16S-726/AF155957/770-1495 | Target | 726 bp PCR amplicon |
| T-bm16S-165/AF155957/310-474 | Target | 165 bp PCR amplicon |
| T-bm16S-157/AF155957/1198-1354 | Target | 157 bp PCR amplicon |
| T-bsDnaK/Z99117/12110-12237 | Target | 128 bp PCR amplicon |
| T-bsEbrA/Z99113/57162-57310 | Target | 149 bp PCR amplicon |
| T-bsFruR/Z99111/96526-96652 | Target | 127 bp PCR amplicon |
| T-bsGrpE/Z99117/13669-13794 | Target | 126 bp PCR amplicon |

TABLE 1-continued

Designation and sequences of oligonucleotides
(SEQ ID NOS 1-54, respectively, in
order of appearance)

| Oligo ID[a] | Function[b] | Sequence[c] |
|---|---|---|
| T-bsSpo0A/Z99116/108693-108839 | Target | 147 bp PCR amplicon |
| T-bsYisY/Z99109/157532-157677 | Target | 146 bp PCR amplicon |

[a]Oligo ID includes the oligo's Name/GenBank accession number/Numbers of first and last nucleotides in the deposited DNA sequence.
[b]Abbreviations: Cmplx - complex; prmr - primer; Unvrsl - universal; Spcfc - specific.
[c]Universal primers and Universal segments of complex primers are shown in bold font.

Materials and Methods 1. 3-D Biochips Manufacturing.

3D polyacrylamide biochips were produced by photopolymerization as described (Guschin et al., 1997). Briefly, 4% acrylamide (acrylamide:bisacrylamide, 19:1) in 40% glycerol, 0.002% methylene blue, 0.012% TEMED, and 0.1 M sodium phosphate buffer, pH 7.0 was prepared. The mixture was applied to an assembled polymerization chamber consisting of a quartz mask (100×100×1.5 mm) pretreated with Repel-Silane™ (LKB, Bromma, Sweden) and then with 0.01% Tween 20 (Fisher Scientific, NJ); two 20-μm thick 2.5×25 mm Teflon spacers; and a 75×25×1 mm glass microscope slide (Corning Micro Slides, Corning, N.Y.) pretreated with Bind-Silane (LKB, Bromma, Sweden) placed on the top of the spacers. He assembled chamber, filled with acrylamide solution was exposed to UV light for 30 min on a 254-nm UV Stratalinker 1800 (Stratagene, La Jolla, Calif.) from a distance 1 in. After photopolymerization the matrix was washed with water to remove non-polymerized acrylamide, dried and kept at room temperature. Each matrix occupies 1 $cm^2$ on a flat surface and comprises 676 polyacrylamide gel elements, each with dimensions of 100×100×20 μm, and 300 μm between the centers of two adjacent elements. Up to four matrixes, called sectors, can be polymerized on a standard microscope slide. Each sector is further subdivided into four quadrants. Aminomodified primers were immobilized to gel elements as described previously (Proudnikov et al., 1998) with some modifications.

Briefly, to generate aldehyde groups on polyacrylamide, standard microscope glass slides containing the matrixes were incubated in 2% trifluoroacetic acid for 10 minutes at room temperature. After a brief rinsing in deionized water ($dH_2O$), the slides were incubated in 0.1 M of $NaIO_4$ for 15 minutes at room temperature, rinsed in $dH_2O$, air-dried for 30 minutes, and treated with Repel Silane for 1 minute at room temperature. The slides were rinsed sequentially in $dH_2O$, 100% ethanol, $dH_2O$, dichloromethane, and $dH_2O$ for 20 seconds per each rinsing; air-dried and used for loading of oligonucleotides within 3 hours after completion of the activation procedure. Equal volumes of 2 mM aqueous solutions of forward and reverse primers from the same pair were mixed, 15 μL of resulting solutions were loaded into an 864 well plate, and the plate was sealed and stored at 4° C. The primers were loaded on activated gel pads by an arrayer made in-house, as was described earlier (Yershov et al., 1996).

Each pair of primers was loaded on 10 adjacent gel pads to generate internal statistics for each separate experiment and improve the accuracy of the quantitative analysis. Immediately after loading, microarrays were placed into a humid chamber and incubated for 30 to 45 min at room temperature to achieve more uniform distribution of the primers in the gel pads. Subsequently, the oligonucleotides were chemically immobilized to the gel pads by incubating the slides in chloroform containing 0.1 M of pyridine borane complex overnight at room temperature. To eliminate the excess of aldehyde groups on polyacrylamide, the slides were incubated in 0.1 M solution of sodium borohydrate for 15 minutes at room temperature. Finally, the slides were washed in 0.1× SSPE and 1.0% Triton X-100 for 30 minutes at 60° C. to remove primers that were not properly immobilized, rinsed in $dH_2O$, and air-dried. The slides were kept dry at room temperature.

2. Synthesis and Chemical Modifications of Oligonucleotides

Automated synthesis of DNA oligonucleotides was performed in-house on 394 DNA/RNA Synthesizer (Applied Biosystems, Foster City, Calif.), using standard phosphoramidite chemistry. After synthesis, the oligonucleotides were purified by reverse-phase HPLC (RP-HPLC). Complex primers that were to be immobilized to the gel pads were modified at the 5'ends with polyethylene glycol linkers with approximate molecular weight of 900 (PEG-900) as described elsewhere (Jaschke et al., 1994).

Fluorescently labeled probes were prepared by conjugating Texas Red sulfonyl chloride fluorescent compound and an oligonucleotide as described elsewhere (Hermanson, 1996). Besides Texas Red, all other suitable fluorescent dyes, such as Marina Blue, Pacific Blue, Oregon Green, FITC, Tetramethylrhodamine, different kinds of Alexa Fluor (Molecular Probes, Eugene, Oreg.), Cy3, Cy5 (Amersham, Piscataway, N.J.), etc. can be used for the probe labeling.

3. Conventional PCR.

PCR reactions were performed in 25 μL containing 1 to 2 units of AmplyTaq DNA Pol, Stoffel fragment (Applied Biosystems, Foster City, Calif.); $MgCl_2$ at a concentration of 2.5 mM; dNTPs mix of four nucleotides at a concentration of 1 mM (Applied Biosystems, Foster City, Calif.); forward and reverse primers at a concentration of 400 nM; and $10^1$ to $10^6$ copies of target DNA. Reactions were carried out for 25 to 30 cycles, with 45 seconds at 94° C., 1 min at annealing temperature, and 45 to 60 seconds at 72° C. Initial activation was done at 94° C. for 3 minutes, and the final cycle was followed by an incubation at 72° C. for 3 minutes. PCR machines used were Eppendorf Mastercycler gradient (Eppendorf, Hamburg, Germany) and MJ Research PTC-220 DNA Engine Dyad (MJ Research.

4. Dual-Phase PCR a. Monoplex PCR

PCR chambers were created by placing in situ frames, 25 μL, (Eppendorf-Brinkmann) on a microscope glass slide, so that the microarrays would be surrounded by the frame. 30 μL of the reaction mix included the following components: $10^5$-

$10^6$ copies of target DNA, 1× reaction buffer (10 mM TrisHCl, pH 8.3, 10 mM KCl), 2.5 mM $MgCl_2$, 250 μM each of the four dNTPs (Applied Biosystems), 40 ng/μL of yeast tRNA (Ambion), 0.5% BSA (Sigma), 400 nM each of universal primers, and 0.2 u/μL of AmplyTaq DNA Pol, Stoffel fragment (Applied Biosystems). Prior to PCR the reaction mix was degassed in Centrivap Concentrator (Labconco, Kansas City, Mo.) at 0.01-0.02 bars for 90 seconds at ambient temperature (5 μL of deionized water was added for each 30 μL of the reaction cocktail to compensate for the evaporation). 25 μL of degassed PCR reaction mix was released on a microarray, and a chamber was sealed with a plastic lid. The microscope slides were placed either on top of the in situ adapter of Eppendorf Mastercycler gradient machine, or into the Twin Tower Block of the MJ Research PTC-200 DNA Engine Dyad machine.

The cycling occurred as follows: initial heating at 93° C. for 3 minutes, then 25 cycles of incubation at 92° C. for 45 seconds, at annealing temperature for 2.5 minutes, at 72° C. for 2.5 minutes; then another 25 cycles at 92° C. for 45 seconds, annealing temperature for 1 minute 15 seconds, and 72° C. for 1 minute 15 seconds, followed by final incubation at 72° C. for 3 minutes.

b. Multiplex PCR

Two important modifications were made to the on-chip PCR protocol. First, the reaction chambers were created by placing 18×18 mm glass cover slips directly on microarrays, and the chambers were sealed by Self-Seal Reagent (MJ Research) present in the reaction mix. Second, PCR reaction on each microarray was performed twice: the first time without universal primers, and the second time with them.

10 μL of the reaction mix containing $10^1$-$10^6$ copies of target DNA, 1× reaction buffer (10 mM TrisHCl, pH 8.3, 10 mM KCl), 2.5 mM $MgCl_2$, 250 μM each of the four dNTPs (Applied Biosystems), 40 ng/μL of yeast tRNA (Ambion), 0.5% BSA (Sigma), 0.8× Self Seal Reagent (MJ Research), and 0.5 u/μL of Stoffel DNA Pol (Applied Biosystems) were degassed as described above and loaded onto the center of a microarray. 18×18 mm No. 1 premium cover glass slips (Fisher Scientific) were placed directly on microarrays, so that the reaction mix would spread evenly between the surfaces without leaving air bubbles under the cover slip.

The reaction was run for 40 cycles: initial denaturing at 93° C. for 3 minutes, then incubation at 92° C. for 45 seconds, incubation at 59° C. for 1.5 minutes, at 72° C.—for 1 minute, and final extension at 72° C. for 3 minutes. After that, the slides were soaked in $dH_2O$ for 5 minutes, the cover slips removed from the microarrays, and the microarrays briefly rinsed in buffer containing 6×SSPE (NaCl, $NaH_2PO_4$—$H_2O$, EDTA) and 1% Tween-20, then washed for 15 minutes in $dH_2O$ at ambient temperature. The slides were air-dried, then used for the second round of PCR, which was essentially the same as the first one, except that that the universal primers at a concentration of 40 nM were added into the reaction mix, and the number of cycles was reduced to 30. Appropriate modifications (scale-up) can be performed to accommodate for larger sample sizes.

4. Treatment with Proteinase K and DNaseI

Proteinase K treatment of slides was done to remove the protein deposits that build up on the surface of microarrays during PCR. The slides were treated at 37° C. for 1.5 hours in PK buffer, containing 10 mM TrisHCl, pH 7.5; 5 mM EDTA, 0.4% SDS, and 100 μg/mL of Proteinase K (Amresco, Solon, Ohio).

DNaseI treatment of genomic DNA samples was done to decrease the size of the DNA fragments. The treatment was done as following. Per each 100 μL of reaction mix, we added 5 μg of genomic DNA; 10 μL of 10× reaction buffer (Ambion, Austin, Tex.), containing 100 mM TrisHCl, pH 7.5, 25 mM $MgCl_2$, and 5 mM $CaCl_2$; and 0.1 units of DNaseI (Ambion, Austin, Tex.). The reaction mix was incubated at 37° C., and 20 μL aliquots were taken at 0-minute, 3-minute, 6-minute, 12-minute, and 18-minute time points. The reaction was stopped by adding EDTA to a final concentration of 10 mM and by placing the tubes on ice. DNaseI was then irreversibly inactivated by incubation of the samples at 75° C. for 7.5 minutes. The DNA was purified by a standard phenol-chloroform extraction procedure and precipitated with two volumes of 100% ethanol.

5. Hybridization

The microarrays were hybridized in a buffer containing 1 M guanidine thiocyanate (FisherScientific, NJ), 50 mM HEPES pH 7.5, 5 mM EDTA, 40 ng/μL of yeast tRNA (Ambion, TX), 0.1% BSA (Sigma, St. Louis, Mo.), and 2.5 nM of reporting probe labeled at the 3'end with Texas Red (Molecular Probes, OR). The slides were incubated at 92° C. for 2 minutes, then at 70° C. for 10 minutes, and left at 30° C. overnight. Prior to image acquisition the excess of the recognizing probe was removed by washing the microarrays in washing buffer containing 6×SSPE and 1% Tween-20 at ambient temperature for 5 minutes. After the image acquisition, the microarrays were incubated in a stripping buffer containing 4.9 M guanidine thiocyanate, 25 mM HEPES pH 7.5, and 0.1% of Triton X-100, at 37° C. for 1 hour. The microarrays were rinsed in $dH_2O$ and kept in $dH_2O$ until the next hybridization.

6. Fluorescent Label Incorporation into DNA During PCR Amplification

Dual-phase PCR was performed as described above with the only modification. Standard mixture of four dNTPs was replaced with a mixture of dATP, dCTP and dGTP at a final concentration of 250 μM each, dTTP at a final concentration 180 μM, and Texas Red Chromatide-12-dUTP (Molecular Probes, Eugene, Oreg.) at a final concentration 20 μM. The thermal cycling conditions were the same as for standard dual-phase PCR described above.

7. Image Acquisition and Analysis

Images of the microarrays were acquired using a fluorescence microscope, CCD camera, and WinView software as previously described (Barskii et al., 1998; Kelly et al., 2002). Briefly, the microscope consists of the following parts. Mercury-quartz lamp as a light source, collector lens, a field stop, heat-protective filter, electromagnetic shutter, exciting filter, interference beamsplitter plate, objectives, cutoff filter, mirror and CCD camera. TEK-512TK CCD camera (Princeton Instruments, NJ) has the following characteristics. Pixel size is 24×24 μm, the dynamic range is 12 bits, the dark noise is 7 electron/(pixel×sec), and the image read-out time is 1.2 sec. When the camera is used with 3.0×0.4 objective, the field is 4×4 mm. The fluorescent intensity of each gel element was quantified from the WinView image using LabView software customized by our laboratory. The score for each gel element was calculated by subtracting the averaged fluorescent intensity of the area immediately surrounding the gel element from the averaged fluorescent intensity of the entire area of the gel element. The scores obtained for gel elements occupied by immobilized primers were called signals, and the scores obtained for empty gel elements were called the background.

The signals obtained from individual gel elements belonging to the same cluster of 10 gel elements were averaged, and the standard deviation and the confidence interval, where α=0.05, were calculated for each sample using Microsoft Excel 2002 software. The numerical values of the obtained confidence intervals were plotted as Y axis error bars. The background value for each quadrant was obtained by averaging scores of at least 10 gel pads unoccupied by the primers. The signals were plotted after correction for the background.

DOCUMENTS CITED

The following documents are incorporated by reference to the extent they relate to protocols used in this disclosure.

Adams C P, Kron S J (1997) Method for performing amplification of nucleic acid with two primers bound to a single solid support. U.S. Pat. No. 5,641,658.

Adams C P, Kron S J (2000) Method for performing amplification of nucleic acid on supports.

Barskii I Y, Grammatin A P, Ivanov A V, Kreindlin E Y, Kotova E Y, Barskii V E Mirabekov A D (1998) Wide-field luminescence microscopes for analyzing biological microchips. J. Opt. Technol., v. 65, pp. 938-941.

Guschin D, Yershov G, Zaslavsky A, Gemmell A, Shick V, Proudnikov D, Arenkov P, Mirzabekov A. (1997) Manual manufacturing of oligonucleotide, DNA and protein microchips. Anal. Biochem., v. 250, pp. 203-211.

Hermanson G T (1996) Texas Red sulfonyl chloride. In Bioconjugate Technique. Ed. by G. T. Hermanson, Academic Press, Inc., pp. 324-326.

Jäschke A., Furste J P, Nordhoff E, Hillenkamp F, Cech D, Erdmann V A (1994) Synthesis and properties of oligodeoxyribonucleotide-polyethylene glycol conjugates. Nucl. Acids Res., v. 22, pp. 4810-4817.

Kelly J J, Chernov B, Tovstanovski I, Mirzabekov A D, Bavykin S G (2002) Radical generating coordination complexes as a tool for rapid and effective fluorescent labeling and fragmentation of DNA or RNA for microarray hybridization. Analyt. Biochem., v. 311, pp. 103-118

Khrapko K, Lysov Yu, Khorlin A, Shick V, Florentiev V, Mirzabekov A (1989) An oligonucleotide hybridization approach to DNA sequencing. FEBS Letters, v. 256, pp. 118-122.

Mikhailovich V M, Lapa S A, Gryadunov D A, Strizhkov B N, Sobolev A Y, Skotnikova O I, Irtuganova O A, Moroz A M, Litvinov V I, Shipina L K, Vladimirskii M A, Chernousova L N, Erokhin V V, Mirzabekov A D (2001) Detection of rifampicin-resistant Mycobacterium tuberculosis strains by hybridization and polymerase chain reaction on a specialized TB-microchip. Bull. Exp. Biol. Med., v. 131, pp. 94-98.

Morris C P, Harris R J (2000) Solid phase amplification process. U.S. Pat. No. 6,017,738.

Proudnikov D, Timofeev E, Mirzabekov A (1998) Immobilization of DNA in polyacrylamide gel for the manufacture of DNA and DNA-oligonucleotide microchips. Anal. Biochem., v. 259, pp. 34-41.

Strizhkov B N, Drobyshev A L, Mikhailovich V M, Mirzabekov A D (2000) PCR amplification on a microarray of gel immobilized oligonucleotides: detection of bacterial toxin- and drug-resistant genes and their mutations. Bio Techniques, v. 29, pp. 844-857.

Sutton R C, Ponticello I S, Cummins T J, Zander D R, Donish W H, Chen PH-D, Findlay J B (1999) Method for nucleic acid amplification and detection using adhered probes. U.S. Pat. No. 5,888,723.

Tillib S V, Strizhkov B N, Mirzabekov A D (2001) Integration of multiple PCR amplification and DNA mutation analyses by using oligonucleotide microchip. Anal. Biochem., v. 292, pp. 155-160.

Yershov G, Barsky V, Belgovskiy A, Kirillov E, Kreinlin E, Ivanov I, Parinov S, Guschin D, Drobishev A, Dubiley S, Mirzabekov A (1996) DNA analysis and diagnostics on oligonucleotide microchips. Proc. Natl. Acad. Sci. USA, v. 93, pp. 4913-4918.

Zlatanova J and Mirzabekov A (2001) Gel-immobilized microarrays of nucleic acids and proteins. In Methods in Molecular Biology, v. 170: DNA Arrays: Methods and Protocols. Ed. by J B Rampal, Humana Press Inc. Totowa, N.J., pp. 17-38.

U.S. Pat. No. 6,090,592.

---

We claim:

1. A method to amplify a target nucleic acid molecule in a sample, the method comprising:
   (a) performing linear multiplex amplification of the target nucleic acid on a support with complex primers and universal primers to obtain modified target nucleic acids;
   (b) releasing the amplified modified target nucleic acid to a liquid phase; and
   (c) performing a dual phase amplification of the modified target nucleic acid molecules in the liquid phase with universal primers and in the support with complex primers.

2. A method to amplify a target nucleic acid molecule in a sample, the method comprising:
   (a) immobilizing a plurality of first and second complex primers to a support;
   (b) annealing a single stranded target nucleic acid molecule to a specific segment of a first complex primer on the support;
   (c) extending the first complex primer to synthesize a first complementary nucleic acid molecule on the support;
   (d) forming a bridge from the first complementary nucleic acid molecule to a specific segment of a second complex primer on the support;
   (e) extending the second complex primer to synthesize a second complementary nucleic acid molecule on the support;
   (f) amplifying the first and second complementary nucleic acid molecules immobilized to the support using unbound universal primers to synthesize a plurality of modified target nucleic acids;
   (g) releasing the modified target nucleic acids to a liquid phase of a reaction chamber;
   (h) amplifying the modified target nucleic acids in the liquid phase of the reaction chamber using unbound universal primers and in the support with the complex primers simultaneously.

3. The method of claim 2, wherein the first complex primer comprises a segment complementary to the target nucleic acid molecule and a universal segment.

4. The method of claim 2, wherein the second complex primer comprises a segment complementary to the first complementary target nucleic acid molecule and a universal segment.

5. The method of claim 2, wherein the universal primers comprise sequences specific to the sequences of the universal segments of the complex primers.

6. The method of claim 2, wherein the plurality of first and second complex primers comprise segments that are complementary to a plurality of target nucleic acid molecules.

7. The method of claim 2, wherein the first and the second complex primers are immobilized to an attachment site that is spatially separated from other pairs of primers.

8. The method of claim 2, wherein the first complex primer is designated forward primer and the second complex primer is designated reverse primer.

9. The method of claim 2 further comprising a method of detecting the amplified nucleic acid molecules in the support comprising detecting the annealed amplified molecules in the support with a probe.

10. The method of claim 9, wherein the probe is selected from the group consisting of nucleic acids, antibodies, and peptides labeled with radioactive isotopes, gold particles, light scattering particles, energy transferring compounds, fluorescent dyes, or luminescent dyes.

11. The method of claim 9, wherein the probe is targeted toward any segment of the amplified nucleic acid molecules.

12. The method of claim 2, wherein the first and second complex primers are about 10 to 100 bases long.

13. The method of claim 2, wherein the universal primers are about 5 to 95 bases long.

14. The method of claim 2, wherein the liquid phase of the reaction chamber is in contact with the support.

15. The method of claim 2 further comprising a method of detecting the amplified nucleic acid molecules in the support comprising:
   (a) incorporating labeled nucleotides during nucleic acid amplification; and
   (b) detecting the labeled nucleotides in the amplified nucleic acid molecules.

16. The method of claim 15, wherein the labeled nucleotides comprise labels selected from the group consisting of fluorescent, luminescent, radioactive, and immunological.

17. The method of claim 2, wherein the support is selected from the group consisting of glass, microbeads, microcanals, gel pads, membranes, metal, plastic and any suitable matrix.

18. A method to amplify a target nucleic acid molecule in a sample using a combination of a plurality of universal primers present in a solution and a plurality of complex primers immobilized to a solid support, wherein the complex primers comprise a 5'-universal segment and a 3'-segment specific to a target nucleic acid in the sample, the method comprising:
   (a) annealing the target nucleic acid molecule reversibly to the solid support via hybridization of the 3'-specific segment of a first immobilized complex primer to the target nucleic acid, where an extension of the first complex primer results in a linear amplification of the target nucleic acid molecule and an irreversible binding of the amplified target nucleic acids to the solid support through the first complex primer;
   (b) forming a bridge between extended first complex primer bound in the solid support and a second complex primer via hybridization of the complementary sequences of the extended first complex primer and a 3'-segment of the second complex primer followed by extension of the second complex primer, resulting in further amplification of the target nucleic acid;
   (c) amplifying the extended first and second complex primers bound to the support using universal primers to synthesize a plurality of modified target nucleic acids;
   (d) releasing the amplified modified targets to the solution, wherein further pseudo-monoplex amplification with universal primers occurs; and
   (e) annealing 3'-end regions of the amplified modified target nucleic acids in solution to the complex primers attached to the solid support resulting in further linear amplification of the modified target nucleic acids bound to the support.

19. The method of claim 18, wherein the plurality of complex primers comprise 3'-segments that are specific to a plurality of different target nucleic acid molecules.

20. The method of claim 18, wherein the universal primers comprise nucleotide sequences that are at least partially identical to the 5'-universal segment of the complex primer.

21. The method of claim 18, wherein the plurality of universal primers comprise more than one specific sequence.

22. The method of claim 18, wherein further detection of the amplified target nucleic acid molecules bound to the solid support comprises hybridization with probes bearing a label selected from the group consisting of fluorescent dyes, luminescent dyes, radioactive isotopes, immunological markers, gold particles, beacon labels, light scattering labels, energy transfer labels.

* * * * *

UNITED STATES PATENT AND TRADEMARK OFFICE
CERTIFICATE OF CORRECTION

PATENT NO. : 7,432,055 B2 Page 1 of 1
APPLICATION NO. : 10/794381
DATED : October 7, 2008
INVENTOR(S) : Alexander Pemov et al.

It is certified that error appears in the above-identified patent and that said Letters Patent is hereby corrected as shown below:

In column 43, claim 1, line 49 should read as follows:

-- (b) releasing the amplified modified target nucleic acids to a liquid phase; and --

Signed and Sealed this

Sixteenth Day of December, 2008

JON W. DUDAS
*Director of the United States Patent and Trademark Office*

SEQUENCE LISTING

```
<160> NUMBER OF SEQ ID NOS: 54

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gctaaatcgg actagctacc cacactggga ctgagacac                              39

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
```

-continued taatccagct acgctgcatc gccagcttat tcaactagca c            41

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gctaaatcgg actagctacc tcatcatgcc ccttatgacc            40

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
taatccagct acgctgcatc cgcgattact agcgattcc            39

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ggattaggtg agattgaggt acaaagagct gcaagacc            38

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
taatccagct acgctgcatc cgcgattact agcgattcc            39

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttttcttctc tccccaatct cgtacaaaga gctgcaagac c            41

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
atcagcaatg ccttctaagt ccgcgattac tagcgattcc            40

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ttttcttctc tccccaatct cgcttccagc ttactgatat cc                           42

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
atcagcaatg ccttctaagt cgttttgttc ttttcctgtg cc                           42

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ttttcttctc tccccaatct caaccatatt cccctgagcc                              40

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
atcagcaatg ccttctaagt cagtaacacg acccctgata g                            41

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ttttcttctc tccccaatct ccgatcaaac aggcaaaaca c                            41

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
atcagcaatg ccttctaagt caatgtaagc tcttcagcgt c                            41

```
<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ttttcttctc tccccaatct cgaagccgac aatgaacaga c                              41

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
atcagcaatg ccttctaagt caggatcaaa ttcctgccct ac                             42

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ttttcttctc tccccaatct caggacagga agacatggaa g                              41

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
atcagcaatg ccttctaagt ctccctcagc ctctctaaaa c                              41

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ttttcttctc tccccaatct cgccgatgat gtgaaagcag                                40

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
atcagcaatg ccttctaagt cgccgcagac agtaaaatca g                              41
```

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gctaaatcgg actagctacc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
taatccagct acgctgcatc                                               20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ttttcttctc tccccaatct c                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
atcagcaatg ccttctaagt c                                             21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
cacactggga ctgagacac                                                19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gccagcttat tcaactagca c                                             21

<210> SEQ ID NO 27
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tcatcatgcc ccttatgacc                                              20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
cgcgattact agcgattcc                                               19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gtacaaagag ctgcaagacc                                              20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
cgcgattact agcgattcc                                               19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gcctaataca tgcaagtcga g                                            21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
tcagtgtcag ttacagacca g                                            21

<210> SEQ ID NO 33
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gtggggagca aacaggatta g                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
acttcacccc aatcatctgt c                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
gcttccagct tactgatatc c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
gttttgttct tttcctgtgc c                                              21

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
aaccatattc ccctgagcc                                                 19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
agtaacacga cccctgatag                                                20

<210> SEQ ID NO 39
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 39
cgatcaaaca ggcaaaacac                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
aatgtaagct cttcagcgtc                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
gaagccgaca atgaacagac                                                  20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
aggatcaaat tcctgcccta c                                                21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
aggacaggaa gacatggaag                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
tccctcagcc tctctaaaac                                                  20

<210> SEQ ID NO 45
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 45
gccgatgatg tgaaagcag                                                      19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
gccgcagaca gtaaaatcag                                                     20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 47
aatggacgaa agtctgacgg                                                     20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 48
tcggattgta ggctgcaact                                                     20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 49
gctcttacgt ttacgatacc g                                                   21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 50
gaatcccgat aagccctttg                                                     20

<210> SEQ ID NO 51
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      Probe

<400> SEQUENCE: 51
tacgtcttag cagacccttc                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 52
ttcaaggctt ctacgagctg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 53
tgtccgttat aagcaacgcc                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Probe

<400> SEQUENCE: 54
cccattgaaa aaccggcaag                                              20
```